United States Patent [19]

Tonks et al.

[11] Patent Number: 5,951,979
[45] Date of Patent: Sep. 14, 1999

[54] SUBSTRATE TRAPPING PROTEIN TYROSINE PHOSPHATASES

[75] Inventors: Nicholas Tonks, Huntington, N.Y.; Andrew J. Flint, Bothell, Wash.

[73] Assignee: Cold Spring Harbor Laboratory, Cold Spring Harbor, N.Y.

[21] Appl. No.: 09/144,925

[22] Filed: Sep. 1, 1998

Related U.S. Application Data

[62] Division of application No. 08/685,992, Jul. 25, 1996.

[51] Int. Cl.[6] .............................. A61K 38/46; C12N 9/16
[52] U.S. Cl. .......................................... 424/94.6; 435/196
[58] Field of Search ............................ 424/94.6; 435/196

[56] References Cited

U.S. PATENT DOCUMENTS

| | | | |
|---|---|---|---|
| 5,352,660 | 10/1994 | Pawson | 514/12 |
| 5,585,233 | 12/1996 | Moller et al. | 435/6 |
| 5,589,375 | 12/1996 | Ullrich et al. | 435/240.2 |

FOREIGN PATENT DOCUMENTS

| | | |
|---|---|---|
| WO 94/21800 | 9/1994 | WIPO. |
| WO 95/06735 | 3/1995 | WIPO. |
| 96/17866 | 6/1996 | WIPO. |

OTHER PUBLICATIONS

Sun, et al., "MKP–1 (3CH134), an Immediate Early Gene Product, Is a Dual Specificity Phosphatase That Dephosphorylates MAP Kinase In Vivo", *Cell* 75:487–493 (1993).
Barford, et al., "Crystal Structure of Human Protein Tyrosine Phosphatase 1B", *Science* 263:1397–1404 (1994).
Songyang, et al., "SH2 Domains Recognize Specific Phosphopeptide Sequences", *Cell* 72:767–778 (1993).
Songyang, et al., "Catalytic specificity of protein–tyrosine kinases is critical for selective signalling", *Nature* 373:536–539 (1995).
Jia, et al., "Structural Basis for Phosphotyrosine Peptide Recognition by Protein Tyrosine Phosphatase 1B", *Science* 268:1754–1758 (1995).
Barford, et al., "Protein tyrosine phosphatases take off", *Nature Struc. Biol.* 2(12):1043–1053 (1995).
Zhang, et al., "Dissecting the catalytic mechanism of protein–tyrosine phosphatases", *Proc. Natl. Acad. Sci. USA* 91:1624–1627 (1994).
Tonks, "Introduction: protein tyrosine phosphatases", *Seminars in Cell Biol.* 4:373–377 (1993).
Cho, et al., "Substrate specificities of catalytic fragments of protein tyrosine phosphatases (HPTPβ, LAR, and CD45) toward phosphotyrosylpeptide substrates and thiophosphotyrosylated peptides as inhibitors", *Protein Sci.* 2:977–984 (1993).
Dechert, et al., "Comparison of the specificity of bacterially expressed cytoplasmic protein–tyrosine phosphatases SHP and SH–PTP2 towards synthetic phosphopeptide substrates", *Eur. J. Biochem.* 231:673–681 (1995).
Ruzzene, et al., "Specificity of T–cell protein tyrosine phosphatase toward phosphorylated synthetic peptides", *Eur. J. Biochem.* 211:289–295 (1993).
Zhang, et al., "Protein Tyrosine Phosphatase Substrate Specificity: Size and Phosphotyrosine Positioning Requirements in Peptide Substrates", *Biochemistry* 33:2285–2290 (1994).
Garton and Tonks, "PTP–PEST: a protein tyrosine phosphatase regulated by serine phosphorylation", *EMBO J.* 13(16):3763–3771 (1994).
Flint, et al., "Multi–site phosphorylation of the protein tyrosine phosphatase, PTP1B: identification of cell cycle regulated and phorbol ester stimulated sites of phosphorylation", *EMBO J.* 12(5):1937–1946 (1993).
Kanner, et al., "The SH2 and SH3 domains of pp60[src] direct stable association with tyrosine phosphorylated proteins p130 and p110", *EMBO J.* 10(7):1689–1698 (1991).
Mayer and Hanafusa, "Mutagenic Analysis of the v–crk Oncogene: Requirement for SH2 and SH3 Domains and Correlation between Increased Cellular Phosphotyrosine and Transformation", *J. Virol.* 64:3581–3589 (1990).
Auvinen, et al., "Ornithine Decarboxylase–and ras–Induced Cell Transformations: Reversal by Protein Tyrosine Kinase Inhibitors and Role of pp130[CAS]", *Mol. Cell. Biol.* 15(12):6513–6525 (1995).
Charbonneau and Tonks, "1002 Protein Phosphatases?", *Annu. Rev. Cell Biol.* 8:463–493 (1992).
Milarski, et al., "Sequence Specificity in Recognition of the Epidermal Growth Factor Receptor by Protein Tyrosine Phosphatase 1B", *J. Biol. Chem.* 268(31):23634–23639 (1993).
Eckstein, Jens W. et al., "Identification of an Essential Acidic Residue in Cdc25 Protein Phosphatase and a General Three–Dimensional Model for a Core Region in Protein Phosphatases", *Protein Science*, 5:5–12 (1996).
Yang, Qing et al., "Cloning and Expression of PTP–PEST", *The Journal of Biological Chemistry*, 268(9):6622–6628 (1993).
Yang, Qing et al., "Cloning and Expression of PTP–PEST, a Novel Human Nontransmembrane Protein Tyrosine Phosphatase", *The Journal of Biological Chemistry*, 268(23):17650 (1993).
Liu, Feng et al., "Direct Binding of the Proline–rich Region of Protein Tyrosine Phosphatase 1B to the Src Homology 3 Domain of p130[Cas]", *The Journal of Biological Chemistry*, 271(49):31290–31295 (1996).

(List continued on next page.)

*Primary Examiner*—Robert A. Wax
*Assistant Examiner*—Einar Stole
*Attorney, Agent, or Firm*—Hamilton, Brook, Smith & Reynolds, P.C.

[57] ABSTRACT

Novel protein tyrosine phosphatases in which the invariant aspartate residue is replaced with an alanine residue and which bind to a tyrosine phosphorylated substrate and are catalytically attenuated are described. Also described are methods of identifying tyrosine phosphorylated proteins which complex with the described protein tyrosine phosphatases.

8 Claims, 6 Drawing Sheets

OTHER PUBLICATIONS

Brautigan, David L. and Pinault, Fran M., "Serine Phosphorylation of Protein Tyrosine Phosphatase (PTP1B) in HeLa Cells in Response to Analogues of cAMP or Diacylglycerol Plus Okadaic Acid", *Molecular and Cellular Biochemistry* 127/128:121–129 (1993).

Flint, Andrew J. et al., "Development of "Substrate–Trapaping" Mutants to Identify Physiological Substrates of Protein Tyrosine Phosphatases", *Proc. Natl. Acad. Sci. U.S.A.,* 94:1680–1685 (1997).

Garton, Andrew J. et al., "Identification of p130$^{cas}$ as a Substrate for the Cytosolic Protein Tyrosine Phosphatase PTP–PEST", *Molecular and Cellular Biology,* 16(11):6408–6418 (1996).

Seely, B. Lynn et al., "Protein Tyrosine Phosphatase 1B Interacts With the Activated Insulin Receptor", *Diabetes,* 45(10):1379–1385 (1996).

Wu, et al., "Probing the Function of Asp128 in the Low Molecular Weight Protein–tyrosine Phosphatase Catalyzed Reaction. A Pre–steady–state and Steady–state Kinetic Investigation", *Biochemistry,* 35:5426–5434 (1996).

Eckstein et al., "Identification of an Essential Acidic Residue in Cdc25 Protein Phosphatase and a General Three–dimensional Model for a Core Region in Protein Phosphatases", *Protein Science,* 5(1):5–12 (1996).

Segel, Iriwn H., "Biochemical Calculations: How to Solve Mathematical Problems in General Biochemistry", Second Edition, John Wiley and Sons, New York, NY, pp. 277–279 (1976).

Zhang, Zhong–Yin, et al., "Expression, Purification, and Physicochemical Characterization of a Recombinant Yersinia Protein Tyrosine Phosphatase", *J. Biol. Chem.* 267(33): 23759–23766 (1992).

Denu, John M., et al., "The Catalytic Role of Aspartic Acid–92 in a Human Dual–Specific Protein–Tyrosine–Phosphatases", *Biochemistry,* 34:3396–3403 (1995).

Zhang, Zhongtao, et al., "Asp$^{129}$ of the Low Molecular Weight Protein Tyrosine Phosphatase Is Involved in Leaving Group Protonation", *J. Biol. Chem.,* 269(42):25947–25950 (1994).

Denu, John M., et al., "Visualization of Intermediate and Transition–State Structures in Protein–Tyrosine Phosphatase Catalysis", Proc. Natl. Acad. Sci. USA, 93:2493–2498 (1996).

FIG. 1A

```
         1         10        20        30        40        50        60
Hum_PTP1B              DFPCRVAKLPKNKN   RNRYRDVSPFDHSRIKLHQE                    DN
Hum_TCPTP              DYPHRVAKFPENRN   RNRYRDVSPYDHSRV LQNA                    EN
Hum_PTP_xi_D1          GITADSSNHPDNKH   KNRYINIVAYDHSRVKLAQL                    AEK
Hum_PTP_zela_D1        GITADSSNHPDNKH   KNRYINIVAYDHSRVKLAQL                    AEK
Hum_PTP_gamma_D        NITAEHSNHPENKH   KNRYINILAYDHSRVKLRPL                    PGK
Dros_PTP99A_D1         DLPCEHSQHPENKR   KNRYLNITAYDHSRVHLHPT                    PGQ
Hum_LCA_D1             QFTWENSNLEVNKP   KNRYANVIAYDHSRVILTSI                    DGV
Hum_PTP_mu_D1          SAPWDSAKKDENRM   KNRYGNIIAYDHSRVRLQTI                    EGD
Hum_PTP_alpha_D1       QATCEAASKEENKE   KNRYVNILPYDHSRVHLTPV                    EGV
Hum_PTP_opsilon_D      QGTFELANKEENRE   KNRYPNILPNDHSRVILSQL                    DGI
Mouso_CD45_D1          KFPIKDARKPHNQN   KNRYVDILPYDYNRVELSEI                    NGD
Hum_SH.PTP2            LYSRKEGQRQENKN   KNRYKNILPFDHTRVVLHDG                    DPN
Hum_SH.PTP1            LHQRLEGQRPENKG   KNRYKNILPFDHSRVILQGR                    DSN
Hum_PTP_bola           NQSCDIALLPENRG   KNRYNNILPYDATRVKLSNV                    DDD
Dros_PTP10D            DQPCTFADLPCNRP   KNRFTNILPYDHSRFKLQPV                    DDD
Hum_SAP.1              SQSQMVASASENNA   KNRYRNVLPYDWSRVPLKPI                    HEE
Ral_PTP_STEP           FVDPKEYDIPGLVR   KNRYKTILPNPHSRVRLTSP                    DPE
Dros_PTP69A_D1         DRTTKNSDLKENAC   KNRYPDIKAYDQTRVKLAVI                    NGL
Hum_MEG2               VGTFHCSMSPGNLE   KNRYGDVPCLDQTRVKLTKR                    SGH
Hum_PTP.PEST           IYPTATGEKEENVK   KNRYKDILPFDHSRVKLTLK                    TPS
Hum_PTPH1              GLAITFAKLPQNLD   KNRYKDVLPYDTTRVLLQGN                    EDY
Hum_PTPH1              PSETSEGDKKHNTS   KNRYTNILPVNHTRVQLKKI                    QDK
Dici_PTP1              QWSTVDSLSNTSYK   KNRYTDIVPYNCTRVHLKRT                    SPS
Fiss_yeast_pyp1        WCCLASSRSTSISR   KNRYTDIVPYDKTRVRLAVP                    KGC
Fiss_yeast_pyp2
Hum_PTP_xi_D2          GITADSSNHPDNKH   KNRYINIVAYDHSRVKLAQL                    AEK
Hum_LCA_D2             TSRFISANLPCNKF   KNRLVNIMPYELTRVCLQPI                    RGV
Hum_PTP_alpha_D2       NDKMRTGNLPANMK   KNRVLQIIPYEFNRVIIPVK                    RGE
Hum_PTP_opsilon_D2     KENMRTGNLPANMK   KARVIQIIPYDFNRVILSMK                    RGQ
Hum_PTP_mu_D2          VEDCSIALLPRNHE   KNRCMDILPPDRCLPFLITI                    DGE
Mouse_CD45_D2          WRTQHIGNQEENKK   KNRNSNVVPYDFNRVPLKHELEMSKESEPESDESSDDSD PMR
Dros_PTP69A_D2         SKSCSVGENEENNM   KNRSQEIIPYDRNRVILTPL                    SGE
Hum_PTP_zeia_D2        QSDYSAALKQCNRE   KNRTSSIIPVERSRVGISSL                    PGM
Hum_PTP_gamma_D2       VECFSAQKECNKE    KNRNSSVVPSERARVGLAPL
Dros_PTP99A_D2         ETNLMAEQVEELKNCTPYLEQQYKNIIQFQPKDIHIASAMKQVNSIKNRGAIFPIEGSRVHLTPKP
Yarsinia_PTP           TNDPRYLQACGGEKI  LNRFRDIQCCRQTAVRAD
                       30       40        50        60

PTP1B66                     →→ →→→→→
                              α1
                            ▲▲▲▲
```

| | 140 | 150 | 160 | 170 | 180 | 190 | 200 |
|---|---|---|---|---|---|---|---|
| Hum_PTP1B | EKGSLKCA | QYWPQKEEKEM | IFEDTNLKLTLISEDIKSYYTVLELE | | | | NLTTQETREI |
| Hum_TCPTP | EKESVKCA | QYWPT DDQEM | LFKETGFSVKLLSEDVKSYYTVLQLE | | | | NINSGETRTI |
| Hum_PTP_xi_D1 | EKGRRKCD | QYWPP ADGSE | EYGN | FLVTQKSVQVLAYYTVFTLRNTKIKKG | | | SQKGRPSGRVV |
| Hum_PTP_zeta_D1 | EKGRRKCD | QYWP ADGSE | EYGN | FLVTQKSVQVLAYYTVFTLRNTKIKKG | | | SQKGRPSGRVV |
| Hum_PTP_gamma_D | EKGRRKCD | MYWP TENSE | EYGN | IIVTLKSTKIHACYTVFSIRNTKVKKGQKGNPKGRQNERVV | | | KKQCNTEKLV |
| Dros_PTP99A_D1 | ERGRRKCD | QYWP KDGVE | TYGV | IQVKLIEEEVMSTYTVLQIKHLKLKK | | | KSGSSEKREL |
| Hum_LCA_D1 | EKSRVKCD | QYWP ARGTE | TCGL | IQVTLLDTVELATYTVFALH | | | KRGVHEIREI |
| Hum_PTP_mu_D1 | EVGRVKCC | KYWP DDTE | IYKD | IKVTLIETELLAEYVIFAVE | | | DMTNRKPQRLI |
| Hum_PTP_alpha_D1 | ERKECKCA | QYWP DQGCW | TYGN | IRVSVEDVTVLVDYTVFCIQQVG | | | PDGCKAPRLV |
| Hum_PTP_epsilon_D | ERKEEKCH | QYWP DQGCW | TYGN | IRVCVEDCVLVDYTIFCIQPQL | | | KKEKATGREV |
| Mouse_CD45_D1 | EGNRNKCA | EYWPSMEEGTR | AFKD | IVTINDHKRCPDYIILNVAH | | | VGQGNTERTV |
| Hum_SH.PTP2 | ERGKSKCV | KYWPD EYALK | EYGV | MRVRNVKESAAHDYTLLKLSK | | | LDNGDLIREI |
| Hum_SH.PTP1 | EKGRNKCV | PYWPE VGMQR | AYGP | YSVTNCGEHDTTEYKLLQVSP | | | EEQLDAHRLI |
| Hum_PTP_bola | EKGRVKCD | HYWPA DQDSL | YYGD | LILQMLSESVLPEWTIFKICG | | | RGSEQRIL |
| Dros_PTP10D | EKGREKCD | QYWPN DTVPV | FYGD | IKVQILNDSHYADWVMFMLC | | | QVEEQKTLSV |
| Hum_SAP.1 | EAGRVKCE | HYWPL DSQPC | THGH | LRVTLVGEEVMENWTVLLLL | | | RGTEERGL |
| Ral_PTP_STEP | EMN EKCT | EYWP EEQV | VHDG | VEITVQKVIHTEDYRLISLR | | | VGEEEDRRQI |
| Dros_PTP69A_D1 | EYNKAKCA | KYWPEKVFDTK | QFGD | ILVKFAQERKTGDYIELNVSKNKAN | | | NTEERQKRQV |
| Hum_MEG2 | EGGRRKCG | QYWPLEKDSRI | RFGF | LTVTNLGVENMNHYKKLEIH | | | FQNESRRL |
| Hum_PTP.PEST | EMGRKKCE | RYWPLYGEDPI | TFAP | FKISCEDEQARTDYFILLLE | | | NTQTGEEHTV |
| Hum_PTPH1 | ERGRTKCH | QYWPD PPDVM | NHGG | FHIQCQSEDCTIAYVSMLVT | | | LTFEGETRDI |
| Hum_PTPH1 | ENCRIKCD | RYWPEQIGGEQFSIYNGNEVFGTYSVELVEVIQCREIITRNIR | | | | | NANFPSVKKV |
| Dici_PTP1 | EAGREMCT | AYWPSNGIGDK QVYGDYCVKQISEENVDNSRFILFEIQ | | | | | DKPNGPPKYI |
| Fiss_yeast_pyp1 | EAGSEKCS | QYWPDNKDHALCLEGG | LRISVQKYETFEDLKVHLFRL | | | | |
| Fiss_yeast_pyp2 | | | | | | | |
| Hum_PTP_xi_D2 | EKGRRKCD | QYWP ADGSE | EYGN | FLVTQKSVQVLAYYTVFTLRNTKIKKG | | | SQKGRPSGRVV |
| Hum_LCA_D2 | EMGREKCH | QYWP AERSA | RYQY | FVVDPMAEYNMPQYILFKVT | | | DARDGQSRTI |
| Hum_PTP_alpha_D2 | ERGQEKCA | QYWP SDGLV | SYGD | ITVELKKEEECESYTVLLVT | | | NTRENKSRQI |
| Hum_PTP_epsilon_D2 | EREQDKCY | QYWP TEGSV | THGE | ITIEIKNDTLSEAISIFLVTLNQPQ | | | ARQEEQVRVV |
| Hum_PTP_mu_D2 | PA QLCP | QYWP ENGVH | RHGP | IQVEFVSADLEEDIISFRIYNA | | | ARPQDGYRMV |
| Mouse_CD45_D2 | NGDQEVCA | QYW GEGKQ | TYGD | MEVEMKDTNRASAYTLFELR | | | HSKRKEPRTV |
| Dros_PTP69A_D2 | D GPRKCP | RYWA DDEVQ | YDH | ILVKYVHSESCPYYTFFYVT | | | NCKIDDTLKV |
| Hum_PTP_zeta_D2 | NMAEDEFV | YWPNKDEPINCESFKVTLMAEEHKCLSNEEKLIIFILE | | | | | ATQDDYVLEV |
| Hum_PTP_gamma_D2 | SLAEDEFV | YWPSREESMNCEAFTVTLISKDRLCLSNEEQIIIFILE | | | | | ATQDDYVLEV |
| Dros_PTP99A_D2 | D INFA | QFWPDEATPIESDHY | RVKFLNKTNKSDYVSFVIQ | | | | SIQDDYELTV |
| Yarsinia_PTP | EIANQRFGMPDYFR | QSGT | YGSITVESKMTQQVGLGDGINMYTLTI | | | | REAGQKTISV |

PTP1Bseq.no. 120 130 140 150 160

PTP1B66

```
                        210        220        230        240        250        260        270
Hum_PTP1B         LHFHYTTwPDF G VPESPASFLNFLFKVRES GSLSPEHG           PVVVHCSAgIGRSGTFC
Hum_TCPTP         SHFHYTTwPDF G VPESPASFLNFLFKVRES GSLNPDHG           PAVIHCSAgIGRSGTFS
Hum_PTP_xi_D1     TQYHYTQwPDM G VPEYSLPVLTFVRKAAYA KRH      AVG       PVVVHCSAgVGRTGTFS
Hum_PTP_zela_D1   TQYHYTQwPDM G VPEYSLPVLTFVRKAAYA KRH      AVG       PVVVHCSAgVGRTGTYI
Hum_PTP_gamma_D   IQYHYTQwPDM G VPEYALPVLTFVRRSSAA RMP      ETG       PVLVHCSAgVGRTGTYI
Dros_PTP99A_D1    YQYHYTNwPDH G TPDHPLPVLNFVKKSSAA NPA      EAG       PIVVHCSAgVGRTGTYI
Hum_LCA_D1        RQFQFMAwPDH G VPEYPTPILAFLRRVKAC NPL      DAG       PMVVHCSAgVGRTGCFI
Hum_PTP_mu_D1     RQFHFTSwPDH G VPYHATGLLGFVRQVKSK SPP      SAG       PLVVHCSAgAGRTGCFI
Hum_PTP_alpha_D1  TQFHFTSwPDF G VPFTPIGMLKFLKKVKAC NPQ      YAG       PIVVHCSAgVGRTGTFV
Hum_PTP_opsilon_D SQLHFTSwPDF G VPFTPIGMLKFLKKVKTL NPV      HAG       PIVVHCSAgVGRTGTFI
Mouso_CD45_D1     THIQFTSwPDH G VPEDPHLLLKLRRRVNAF SNF      FSG       PIVVHCSAgVGRTGTYI
Hum_SH.PTP2       WQYHFRTwPDH G VPSDPGGVLDFLEEVHHK QESIMDAG           PVVVHCSAgIGRTGTFI
Hum_SH.PTP1       WHYQYLSwPDH G VPSEPGGVLSFLDQINQR QESLPHAG           PIIVHCSAgIGRTGTII
Hum_PTP_bola      RHFHYTVwPDH G VPETTQSLIQFVRTVRDY INRSPGAG           PTVVHCSAgVGRTGTFI
Dros_PTP10D       RHFHFTTwPDF G VPNPPQTLVRFVRAFRDR ICA      EQR       PIVVHCSAgVGRSGTFI
Hum_SAP.1         RQFHYQAwPDH G VPSSPDTLLAFWRMLRQW LDQTMEGG           PPIVHCSAgVGRTGTLI
Ral_PTP_STEP      KHYWFTSwPDQ K TPDRAPPLLHLVREVEEAAQQEGPHCS           PIIVHCSAgIGRTGCFI
Dros_PTP69A_D1    TQYHYLTwKDF M APEHPHGIIKFIRQINSVYSLQ     RG         PILVHCSAgVGRTGTLV
Hum_MEG2          THFQFLSwPDY G VPSSAASLIDFLRVVRNQQSLAVSNMGARSKGQCPEPPIVVHCSAgIGRTGTFC
Hum_PTP.PEST      YQFHYVNwPDH D VPSSFDSILDMISLMRKYQEHE     DV         PICIHCSAgCGRTGAIC
Hum_PTPH1         THLQYVAwPDH G VPSSFDLEFVNYVRSLRVDSE                 PVLVHCSAgIGRTGTFC
Dici_PTP1         TQYQYEGwPDH N IPDDSSDFLEFVNYVRSLRVDSE               RNVPIIVHCSAgVGRTGTFC
Fiss_yeast_pyp1   HHYQYPNwSDC N SPENVKSMVEFLKYVNNSHGSG                 NTIVHCSAgVGRTGTFI
Fiss_yeast_pyp2   HHFWVHTwFD  K THPDIESITGLIRCIDKVPNDG                 PMFVHCSAgVGRTGTFI
Hum_PTP_xi_D2     TQYHYTQwPDM G VPEYSLPVLTFVRKAAYA KRH      AVG       PVVVHCSAgVGRTGTYI
Hum_LCA_D2        RQFQFTDwPEQ G VPKTGEGFIDFIGQVHKT KEQFGQDG           PITVHCSAgVGRTGVFI
Hum_PTP_alpha_D2  RQFHFHGwPEV G IPSDGKGMISIIAAVQKQ QQQ      SGNH      PITVHCSAgAGRTGTFC
Hum_PTP_opsilon_D2 RQFHFHGwPEI G IPAEGKGMIDLIAAVQKQ QQQ     TGNH      PITVHCSAgAGRTGTFI
Hum_PTP_mu_D2     QQFQFLGwPMYRD TPVSKRSFLKLIRQVDKWQEEYNGGEG           PTVVHCLNGGGRSGTFC
Mouse_CD45_D2     YQYQCTTwKGE E LPAEPKDLVSMIQDLKQKLPKASPEGMKYH         KHASILVHCRDgSQQTGLFC
Dros_PTP69A_D2    TQFQYNGwPTVDGEVPEVCRGIIELVDQAYNHYKNNKNSGC             RSPLTVHCSLgTDRSSIFV
Hum_PTP_zeia_D2   RHFQCPKwPN    PDSPISKTFELISVIKEEAANR DG             PMIVHDEHgGVTAGTFC
Hum_PTP_gamma_D2  RHFQCPKwPN    PDAPISSTFELINVIKEEALTR DG             PTIVHDEYgAVSAGMLC
Dros_PTP99A_D2    KMLHCPSwPEM   SNPNSIYDFIVDVHERCNDY   RNG            PIVIVDRYgGAQACTFC
Yarsinia_PTP      PVVHVGNwPDQTAVSSEVTKALASLVDQTAETKRNMYESKGSSAVADDSKLRPVIHCRAgVGRTAQLI
PTP1Bseq.no.         180        190        200         210        220

β9                      α3                 β10
PTP1B66
```

```
                      280              290              300              310              320              330        340
Hum_PTP1B           LADTCLLLMDKR       KDPSSVDI         KKVLLEMRKFRMG    LIQTADQLRFSYLAVIEGAKFIMGD
Hum_TCPTP           LVDTCLVLMEKG       DD               KQVLLNMRKYRMG    LIQTPDQLRFSYMAIIEGAKCIKGDSS
Hum_PTP_xi_D1       VLDSMLQQIQHE       GT               VNI              FGFLKHIRSQRNY    LVQTEEQYVFIHDTLVEAILSKETEV
Hum_PTP_zeta_D1     VLDSMLQQIQHE       GT               VNI              FGFLKHIRSQRNY    LVQTEEQYVFIHDTLVEAILSKETEV
Hum_PTP_gamma_D     VIDSMLQQIKDK       ST               VNV              LGFLKHIRTQRNY    LVQTEEQYIFIHDALLEAILGKETEV
Dros_PTP99A_D1      VLDAMLKQIQQK       NI               VNV              FGFLRHIRAQRNF    LVQTEDQYIFLHDALVEAIASGETNL
Hum_LCA_D1          VIDAMLERMKHE       KT               VDI              YGHVTCMRSQRNY    MVQTEDQYVFIHEALLEAATCGHTEV
Hum_PTP_mu_D1       VIDIMLDMAERE       GV               VDI              YNCVRELRSRRVN    MVQTEEQYVFIHDAILEACLCGDTSV
Hum_PTP_alpha_D1    VIDAMLDMMHTE       RK               VDV              YGFVSRIRAQRCQ    MVQTDMQYVFIYQALLEHYLYGDTEL
Hum_PTP_opsilon_D   VIDAMMAMMHAE       QK               VDV              FEFVSRIRNQRPQ    MVQTDMQYTFIYQALLEYYLYGDTEL
Mouso_CD45_D1       GIDAMLEGLEAE       GK               VDV              YGYVVKLRRQRCL    MVQVEAQYILIHQALVEYNQFGETEV
Hum_SH.PTP2         VIDILIDIIREK       GVDCDIDV         PKTIQMVRSQRSG    MVQTEAQYRFIYMAVQHYIETLQRRI
Hum_SH.PTP1         VIDMLMENISTK       GLDCDIDI         QKTIQMVRAQRSG    MVQTEAQYKFIYVAIAQFIETTKKKL
Hum_PTP_bola        ALDRILQQLDSK       DS               VDI              YGAVHDLRLHRVH    MVQTECQYVYLHQCVRDVLRARKLRS
Dros_PTP10D         TLDRILQQINTS       DY               VDI              FGIVYAMRKERVW    MVQTEQQYICIHQCLLAVLEGKENIVGP
Hum_SAP.1           ALDVLLRQLQSE       GL               LGP              FSFVRKMRESRPL    MVQTEAQYVFLHQCICGSSNSQPRPQPR
Ral_PTP.STEP        ATSICCQQLRRE       GV               VDI              LKTTCQLRQDRGG    MIQTCEQYQFVHHAMSLY
Dros_PTP69A_D1      ALDSLIQQLEEE       DS               VSI              YNTVCDLRHQRNF    LVQSLKQYIFLYRALLDTGTFGNTDI
Hum_MEG2            SLDICLAQLEEL       GT               LNV              FQTVSRMRTQRAF    SIQTPEQYYFCYKAILEFA
Hum_PTP.PEST        AIDYTWNLLKAG       KIPEEFNV         IYP              LDIVRKMRDQRAM    AVQTKEQYELVHRAIAQLFEKQLQLY
Hum_PTPH1           TMETAMCLITERN      LP               IYP              LDIVRKMRDQRAM    MVQTSSQYKFVCEAILRVY
Dici_PTP1           TAVIMMKKLDHYFKQLDYNSRIDFNL           FSIVLKLREQRPG    MVQQLEQYLFCYKTILDEIYHRLNC
Fiss_yeast_pyp1     VLDTILRFPESKLSGFNPSVADSSDVVFQLVDHIRKQRMK              MVQTFTQFKYYD     LIDSL
Fiss_yeast_pyp2     AVDQILOVPKNILPK TTNLEDSKDFIFNCVNSLRSQRMK              MVQNFEQFKFLYD    VVDYL
Hum_PTP_xi_D2       VLDSMLQQIQHE       GT               VNI              FGFLKHIRSQRNY    LVQTEEQYVFIHDTLVEAILSKETEV
Hum_LCA_D2          TLSIVLERMRYE       GV               VDM              FQTVKTLRTQRPA    MVQTEDQYQLCYRAALEYL
Hum_PTP_alpha_D2    ALSTVLERVKAE       GI               LDV              FQTVKSLRLQRPH    MVQTLEQYEFCYKVVQEYI
Hum_PTP_opsilon_D2  ALSNILERVKAE       GL               LDV              FQAVKSLRLQRPH    MVQTLEQYEFCYKVVQDFI
Hum_PTP_mu_D2       AISIVCEMLRHQ       RT               VDV              FHAVKTLRNNKPN    MVDLLDQYKFCYEVALEYLNSG
Hum_PTP_opsilon_D2  ALFNLLESAETE       DV               VDV              FQVVKSLRKARPG    VVCSYEQYQFLYDIIASIYPAQNGQV
Mouse_CD45_D2       AMCILVQHLRLE       KC               VDI              CATTRKLRSQRTG    LINSYAQYEFLHRAIINY
Dros_PTP69A_D2      ALTTLMHQLEKE       NS               VDV              YQVAKMINLMRPG    VFADIEQYQFLYKVILSLVSTRQEEN
Hum_PTP_zeta_D2     ALTTLSQQLENE       NA               VDV              FQVAKMINLMRPG    VFTDIEQYQFIYKAMLSLVSTKENGN
Hum_PTP_gamma_D2    AISSLAIEMEYC       ST               ANV              YQYAKLYHNKRPG    VWTSSEDIRVIYN    ILSFLPGNLNLLKR
Dros_PTP99A_D2      GAMCMNDSRNSQ                        LSV              EDMVSOMRVQRNG    MVQKDEQLDVLIK    LAE
Yarsinia_PTP
PTP1Bseq.no.          230              240              250              260              270              280

PTP1B66              >>>>>>>       >>>>>>>        >>>>>          >>>>>>>>>>      >>>>>>>>>>>
                        α4              α5             α5               α6

▲
```

Vmax and Km of 37kDa-PTP1B Mutants Toward RCML

| Enzyme | Vmax (nmol/min/mg) | Km (nM) | Kcat (min⁻¹) |
|---|---|---|---|
| wild type | 60200 | 102 | 2244 |
| Tyr 46 → S | 4120 | 1700 | 154 |
| → L | 4160 | 1700 | 155 |
| Glu 115 → A | 5700 | 45 | 212 |
| → D | 5900 | 20 | 220 |
| Lys 116 → A | 68600 | 150 | 2557 |
| Lys 120 → A | 19000 | 80 | 708 |
| Asp 181 → A | 0.61 | ≤126 | 0.023 |
| → E | 97 | 10 | 3.6 |
| His 214 → A | 700 | 20 | 26 |
| Cys 215 → S | 0.026 | | 0.00097 |
| Arg 221 → K | 11 | 80 | 0.41 |
| → M | 3.3 | 1060 | 0.12 |
| Gln 262 → A | 720 | 9 | 27 |

FIG. 2

SUBSTRATE TRAPPING PROTEIN TYROSINE PHOSPHATASES

RELATED APPLICATIONS

This application is a Divisional under 37 C.F.R. §1.53(b) of prior U.S. application Ser. No. 08/685,992, filed Jul. 25, 1996, the contents of which are incorporated herein by reference in their entirety.

FUNDING

The invention was supported, in whole or in part, by grant 5-RO1-CA53840-05 from the National Institutes of Health. The U.S. Government has certain rights in the invention.

BACKGROUND OF THE INVENTION

The protein tyrosine phosphatase (PTP) family of enzymes consists of more than 500 structurally diverse proteins which have in common the highly conserved 250 amino acid PTP catalytic domain, but which display considerable variation in their non-catalytic segments (Charbonneau and Tonks, *Annu. Rev. Cell Biol.* 8:463–493 (1992); Tonks, *Semin. Cell Biol.* 4:373–453 (1993)). This structural diversity presumably reflects the diversity of physiological roles of individual PTP family members, which in certain cases have been demonstrated to have specific functions in growth, development and differentiation (Desai et al., *Cell* 84:599–609 (1996); Kishihara et al., *Cell* 74:143–156 (1993); Perkins et al., *Cell* 70:225–236 (1992); Pingel and Thomas, *Cell* 58:1055– 1065 (1989); Schultz et al., *Cell* 73:1445–1454 (1993)). Although recent studies have also generated considerable information regarding the structure, expression and regulation of PTPs, the nature of the tyrosine phosphorylated substrates through which the PTPs exert their effects remains to be determined. Studies with a limited number of synthetic phosphopeptide substrates have demonstrated some differences in substrate selectivity of different PTPs (Cho et al., *Protein Sci.* 2: 977–984 (1993); Dechert et al., *Eur. J. Biochem.* 231:673–681 (1995)), and have indicated preferences for certain amino acid residues at particular positions around the phosphorylated tyrosine residue (Ruzzene et al., *Eur. J. Biochem.* 211:289–295 (1993); Zhang et al., *Biochemistry* 33:2285–2290 (1994)). This indicates that PTPs display a certain level of substrate selectivity in vitro, although the physiological relevance of the substrates used in these studies is unclear.

SUMMARY OF THE INVENTION

As described herein, the substrate specificity of mammalian protein tyrosine phosphatases (PTPs) has been investigated using a novel substrate trapping approach in which mutant or altered forms of the mammalian PTP, also referred to as substrate trapping PTPs, are used to bind (trap) one or more substrates of the PTP. Binding of the substrate trapping PTP with a substrate of the PTP results in the formation of a complex which can be readily observed, and, if desired, isolated, and characterized. The mutant forms of the PTPs have attenuated catalytic activity (lack catalytic activity or have reduced catalytic activity) relative to the wild type PTP but retain the ability to bind tyrosine phosphorylated substrate(s) of the wild type PTP.

The methods of the present invention are specifically exemplified herein with respect to the phosphatases PTP1B and PTP-PEST; however, it is understood that the invention is not limited to these specific PTPs but is applicable to all members of the PTP family. In order to identify potential substrates of PTP1B and PTP-PEST, mutant (i.e., altered or substrate trapping) forms of PTP1B and PTP-PEST were generated which were catalytically attenuated but retained the ability to bind substrates. These mutant PTPs associated in stable complexes with proteins which were identified by immunoblotting as p210 bcr:ab1 and $p_{130}^{cas}$, respectively. These associations were observed in lysates from several cell lines and in transfected COS cells, indicating that p210 bcr:ab1 and $p130^{cas}$ represent major physiologically relevant substrates for PTP1B and PTP-PEST.

These results provide the first demonstration of PTPs having inherently restricted substrate specificity in vivo. The methods used to identify p210 bcr:ab1 and $p130^{cas}$ as specific substrates for PTP1B and PTP-PEST, respectively, are generally applicable to any member of the PTP family, of which approximately 500 members have currently been reported, and can be used to determine the physiological substrates of other members of the PTP family.

One embodiment of the invention relates to novel mutant PTPs in which the invariant aspartate residue is replaced with an amino acid which does not cause significant alteration of the Km of the enzyme but which results in a reduction in Kcat to less than 1 per minute (less than 1 $min^{-1}$). These PTPs retain the ability to form a complex with, or bind, their tyrosine phosphorylated substrates, but are catalytically attenuated. In one embodiment, the invention relates to the phosphatase PTP1B in which the invariant aspartate residue at position 181 is replaced with alanine (D181A). In another embodiment the invention relates to the phosphatase PTP-PEST in which the invariant aspartate residue at position 199 is replaced with an alanine (D199A). Another embodiment of the invention relates to a PTP-PEST phosphatase in which the cysteine residue at position 231 is replaced with a serine (C231S). The invention also relates to other mutant or substrate trapping PTPs in which the invariant aspartate residue is replaced with or changed to another amino acid residue, such as alanine. The invariant aspartate residue can be identified in other PTPs by aligning the PTP nucleotide sequence with the nucleotide sequence of a PTP for which the location of the invariant aspartate residue is known.

The invention also relates to a method of identifying a tyrosine phosphorylated substrate of a protein tyrosine phosphatase. According to one embodiment of the present invention, a tyrosine phosphorylated protein of interest is combined with one or more PTP(s) in which the invariant aspartate residue is replaced with an amino acid which does not cause significant alteration of the Km of the enzyme but which results in a reduction in Kcat to less than 1 per minute (less than 1 $min^{-1}$), and the presence or absence of a complex between the protein and the PTP(s) is determined. Presence of a complex in the combination indicates that the tyrosine phosphorylated protein is a substrate of the PTP. The PTP DA mutant binds to or complexes with its substrate but does not dephosphorylate it (or does so very slowly), thereby allowing the complex to be observed and, optionally, isolated and identified. In a particular embodiment of the invention, the invariant aspartate is replaced with an alanine residue (a PTP DA mutation or alteration)

In an alternative embodiment of the present invention, a PTP of interest in which the invariant aspartate residue is replaced with an amino acid which does not cause significant alteration of the Km of the enzyme but which results in a reduction in Kcat to less than 1 per minute (less than 1 $min^{-1}$), is combined with one or more tyrosine phosphorylated proteins, and the presence or absence of a complex between the protein(s) and the PTP is determined. Presence of a complex in the combination indicates that the tyrosine phosphorylated protein is a substrate of the PTP. The PTP DA mutant binds to or complexes with its substrate but does not dephosphorylate it (or does so very slowly), thereby allowing the complex to be observed, and, optionally, isolated and identified. In one embodiment of the invention, the invariant aspartate residue is replaced with an alanine residue (a PTP DA mutation or alteration)

The present invention also relates to a method of identifying a tyrosine phosphorylated substrate of a protein tyrosine phosphatase wherein more than one tyrosine phosphorylated protein of interest is combined with more than one PTP of interest in which the invariant aspartate residue is replaced with an amino acid which does not cause significant alteration of the Km of the enzyme but which results in a reduction in Kcat to less than 1 per minute (less than 1 $min^{-1}$) (e.g., the invariant aspartate is replaced with an alanine residue). Complexes formed in the combination can be isolated and the component PTP and substrate can be identified.

The invention also pertains to a method of reducing the activity of a tyrosine phosphorylated protein, comprising administering to a mammal a PTP in which the invariant aspartate residue is replaced with an amino acid which does not cause significant alteration of the Km of the enzyme but which results in a reduction in Kcat to less than 1 per minute (less than 1 $min^{-1}$) (e.g., the invariant aspartate is replaced with an alanine residue) and which forms a complex with the tyrosine phosphorylated protein. The PTP mutant binds to the phosphorylated protein without dephosphorylating it, thereby inhibiting the activity of the protein and reducing its downstream effects.

For example, the invention relates to a method of reducing the transforming effects of oncogenes associated with $p130^{cas}$, a substrate of PTP-PEST, comprising administering to a mammal wild type PTP-PEST or PTP-PEST in which the invariant aspartate residue is replaced with an alanine residue. Wild type PTP-PEST binds and dephosphorylates $p130^{cas}$, thereby negatively regulating its downstream effects. DA mutants of PTP-PEST bind but do not dephosphorylate $p130^{cas}$ (or dephosphorylate it at a reduced rate); the substrate is thus tied up in the complex with the substrate trapping form of PTP-PEST and cannot exert its downstream effects. Similarly, the invention relates to a method of reducing the formation of signalling complexes associated with $p130^{cas}$, particularly those signalling complexes which induce mitogenic pathways, comprising administering to a mammal wild type PTP-PEST or PTP-PEST in which the invariant aspartate residue is replaced with an alanine residue.

The present invention also relates to assays for identifying agents which alter, e.g., enhance or inhibit, the interaction between a PTP and its phosphorylated substrate. Agents identified by these assays can be agonists (e.g., agents which enhance or increase the activity of the PTP) or antagonists (e.g., agents which inhibit or decrease the activity of the PTP) of PTP activity. The agent may be an endogenous physiological substance or may be a natural or synthetic drug, including small organic molecules.

For example, the tyrosine phosphorylated substrate of a PTP can be identified by the methods described herein. An enzymatic activity assay utilizing the wild type PTP can be carried out in the presence of an agent to be tested, and the resulting amount of enzyme activity can be compared with the amount of enzyme activity in the absence of the agent to be tested. A decrease in the enzymatic activity in the presence of the agent to be tested indicates that the agent inhibits the interaction between the PTP and its substrate. Conversely, an increase in the enzymatic activity in the presence of the agent to be tested indicates that the agent enhances the interaction between the PTP and its substrate.

Alternatively, a competitive binding assay can be carried out utilizing the mutant PTP in the presence of an agent to be tested, and the resulting extent of binding of the mutant PTP to its substrate can be compared with the extent of binding in the absence of the agent to be tested. A decrease in the extent of binding in the presence of the agent to be tested indicates that the agent inhibits the interaction between the PTP and its substrate. Conversely, an increase in the extent of binding in the presence of the agent to be tested indicates that the agent enhances the interaction between the PTP and its substrate.

Thus, the compositions and methods described herein are useful in identifying the tyrosine phosphorylated substrates of members of the PTP family of phosphatases, as well as in regulating the activity of identified substrates. The compositions and methods described herein are also useful for identifying tyrosine phosphorylated proteins which are related to a particular disease or disorder, and to methods of screening for modulators which enhance or inhibit the PTP/substrate interaction for use in therapeutic applications.

BRIEF DESCRIPTION OF THE DRAWINGS

FIGS. 1A–1E show a multiple sequence alignment of the catalytic domains of PTPs (SEQ ID NOS. 1–35). Cytosolic eukaryotic PTPs and domain 1 of RPTPs are combined into one group domains 2 of RPTPs are in a second group and the Yersinia PTP is in a third. Invariant residues shared among all three groups are shown in lower case. Invariant and highly conserved residues within a group are shown in italics and bold, respectively. Within the Yersinia PTP sequence, residue that are either invariant or highly conserved between the cytosolic and RPTP domain sequences are italics and bold, respectively. The position of residues of PTP1B that interact with the peptide are indicated with a small arrowhead, and the residue numbering at the bottom of the alignment corresponds to that for PTP1B.

FIG. 2 shows the Vmax and Km of various PTP1B mutants toward RCML.

DETAILED DESCRIPTION OF THE INVENTION

Figure 1B:

The PTP family of enzymes contains a common evolutionarily conserved segment of approximately 250 amino acids known as the PTP catalytic domain. Within this conserved domain is a unique signature sequence motif, [I/V]HCXAGXXR[S/T]G (SEQ ID NO: 36), that is invariant among all PTPs. The cysteine residue in this motif is invariant in members of the family and is known to be essential for catalysis. It functions as a nucleophile to attack the phosphate moiety of the incoming substrate. If the cysteine residue is altered by site-directed mutagenesis to serine (CS mutants) or alanine (CA mutants), the resulting PTP is catalytically attenuated but retains the ability to complex with, or bind, its substrate, at least in vitro. These results have been confirmed relative to MKP-1, a member of the PTP family (Sun et al., *Cell* 75:487–493 (1993)), as well as other PTPs. However, although these CS mutants can in general bind effectively to phosphotyrosyl substrates in vitro, in many cases such complexes cannot be isolated in vivo. Thus, the CS mutants are limited in their applicability and cannot be used to isolate all combinations of PTPs and substrates.

The crystal structures of PTP1B alone (Barford, et al., Science 263:1397–1404 (1994)) and in a complex with a phosphotyrosine-containing peptide (Jia et al., Science 268:1754–1758 (1995)) were recently determined. These structures indicated twenty seven invariant residues (Barford et al., 1994), one of which is an aspartate residue. This aspartate residue is invariant across the catalytic domains of PTP family members. That is, if the amino acid sequences of the PTP family members are aligned, the aspartate residue is present in each PTP at a corresponding location, although the position numbers may be different due to the shifts required to maximize alignment (see FIG. 1 (from Barford et al., Nature Struc. Biol. 2:1043–1053 (1995)) for an alignment of various PTP sequences). Sequences for which the alignment has not yet been published can readily be aligned with other known PTP sequences, e.g., utilizing available computer software such as GENEWORKS.

Thus, mutant PTPs other than those specifically described herein can readily be made by aligning the amino acid sequence of the PTP catalytic domain with those described herein, identifying the invariant aspartate residue, and changing the residue by site-directed mutagenesis. Although the specific examples of PTP mutants described herein are aspartate to alanine mutants (DA mutants), it is understood that the invention is not limited to changes of aspartate to alanine. The invariant aspartate residue can be changed, e.g., by site-directed mutagenesis, to any amino acid which does not cause significant alteration of the Km of the enzyme but which results in a reduction in Kcat to less than 1 per minute (less than 1 min$^{-1}$). For example, the invariant aspartate residue can be changed or mutated to an alanine, valine, leucine, isoleucine, proline, phenylalanine, tryptophan, methionine, glycine, serine, threonine, cysteine, tyrosine, asparagine, glutamine, lysine, arginine or histidine.

As described herein, pervanadate-treated cells were used as an abundant source of tyrosine phosphorylated proteins to investigate the substrate specificity of PTP-PEST. PTP-PEST is an 88 kDa cytosolic PTP (Charest et al., Biochem. J. 308:425–432 (1995); den Hertog et al., Biochem. Biophys. Res. Commun. 184:1241–1249 (1992); Takekawa et al., Biochem. Biophys. Res. Commun. 189:1223–1230 (1992); Yang et al., J. Biol. Chem. 268:6622–6628 (1993); Yang et al., J. Biol. Chem. 268:17650 (1993)) which is expressed ubiquitously in mammalian tissues (Yi et al., Blood 78: 2222–2228 (1991)), and which exhibits high specific activity when assayed in vitro using artificial tyrosine phosphorylated substrates (Garton and Tonks, EMBO J. 13:3763–3771 (1994)). It has previously been demonstrated that PTP-PEST is subject to regulation via phosphorylation of Ser39 in vitro and in vivo. This modification is catalyzed by both protein kinase C (PKC) and protein kinase A (PKA), and results in reduced enzyme activity as a consequence of an increase in the Km of the dephosphorylation reaction (Garton and Tonks, EMBO J. 13:3763–3771 (1994)). It appears likely that further regulatory mechanisms exist for PTP-PEST, since this enzyme would be expected to exert a considerable negative influence on the tyrosine phosphorylation state of cytosolic substrates of tyrosine kinases. One possibility is that this influence could be limited by the substrate specificity of PTP-PEST.

The substrate specificity of PTP 1B was investigated utilizing the same methods outlined for PTP-PEST, with the exception that the cells were not treated with pervanadate. A combination of in vitro dephosphorylation and substrate trapping experiments were used to study the substrate interactions of PTP1B and PTP-PEST. The substrate trapping methods outlined herein are generally applicable to any PTP by virtue of the shared invariant aspartate residue, and should therefore prove useful in delineating the substrate preference of other PTP family members. In particular, the use of mutant, catalytically impaired PTPs to trap, and thereby isolate, potential substrates will greatly facilitate the identification of physiologically important substrates for individual PTPs, leading to improved understanding of the roles of these enzymes in regulation of cellular processes.

One embodiment of the invention relates to novel PTPs in which the invariant aspartate residue is replaced with an amino acid which does not cause significant alteration of the Km of the enzyme but which results in a reduction in Kcat to less than 1 per minute (less than 1 min$^{-1}$). These PTPs retain the ability to form a complex with, or bind, their tyrosine phosphorylated substrates but are catalytically attenuated. As defined herein, "attenuated" activity is intended to mean that the phosphatase retains a similar Km to that of the wild type phosphatase but has a Vmax which is reduced by a factor of at least $10^4$ relative to the wild type enzyme. This includes catalytic activity which is either reduced or abolished relative to the wild type PTP. For example, the invariant aspartate residue can be changed or mutated to an alanine, valine, leucine, isoleucine, proline, phenylalanine, tryptophan, methionine, glycine, serine, threonine, cysteine, tyrosine, asparagine, glutamine, lysine, arginine or histidine.

The novel PTPs described herein, in which the invariant aspartate residue is replaced with an amino acid which does not cause significant alteration of the Km of the enzyme but which results in a reduction in Kcat to less than 1 per minute (less than 1 min$^{-1}$), can also comprise other mutations, particularly those which assist in stabilizing the PTP/substrate complex. For example, a mutation of the [serine/threonine] residue in the signature motif to an alanine residue changes the rate-determining step of the dephosphorylation reaction from the formation of the transition state to the break down of the transition state, thereby stabilizing the PTP/substrate complex. Such mutations may be valuably combined with the replacement of the invariant aspartate residue, particularly assisting in stabilizing the complex and facilitating the observation and isolation of the complex.

PTPs suitable for use in the invention include any PTP which has an invariant aspartate residue in a corresponding position. As defined herein, a phosphatase is a member of the PTP family if it contains the signature motif [I/V]HCXAGXXR[S/T]G. Dual specificity PTPs, i.e., PTPs which dephosphorylate both phosphorylated tyrosine and phosphorylated serine or threonine, are also suitable for use in the invention. Appropriate PTPs include, but are not limited to, PTP1B, PTP-PEST, PTP$_\gamma$, MKP-1, DEP-1, PTPµ, PTPX1, PTPX10 and PTPH1.

In one embodiment, the invention relates to the phosphatase PTP1B in which the aspartate residue at position 181 is replaced with alanine (D181A). In another embodiment the invention relates to the phosphatase PTP-PEST in which the invariant aspartate residue at position 199 is replaced with an alanine (D199A). Another embodiment of the invention relates to a PTP-PEST phosphatase in which the cysteine residue at position 231 is replaced with a serine (C231S).

The invention also relates to a method of identifying a tyrosine phosphorylated protein which is a substrate of a particular protein tyrosine phosphatase. According to one embodiment of the present invention, a tyrosine phosphorylated protein of interest is combined with at least one PTP in which the invariant aspartate residue is replaced with an amino acid which does not cause significant alteration of the Km of the enzyme but which results in a reduction in Kcat to less than 1 per minute (less than 1 min$^{-1}$) (e.g., an alanine residue), and the presence or absence of a complex between the protein and the PTP is determined. Presence of a complex in the combination indicates that the tyrosine phosphorylated protein is a substrate of the PTP. The PTP DA mutant (substrate trapping mutant) binds to or complexes with its substrate but does not dephosphorylate it (or does so very slowly), thereby allowing the complex to be isolated and identified.

The phosphorylated protein/PTP complex may be isolated by conventional isolation techniques as described in U.S. Pat. No. 5,352,660 to Pawson, including salting out, chromatography, electrophoresis, gel filtration, fractionation, absorption, polyacrylamide gel electrophoresis, agglutination, or combinations thereof. Furthermore, to facilitate the determination of the presence of the protein/PTP complex, antibodies against the PTP or the phosphorylated protein can be used, as well as labelled PTPs and/or labelled phosphorylated substrates. The PTP or phosphorylated protein can be labelled with various enzymes, fluorescent materials, luminescent materials and radioactive materials. Examples of suitable enzymes include, but are not limited to, horseradish peroxidase, biotin, alkaline phosphatase, β-galactosidase and acetylcholinesterase. Examples of suitable fluorescent materials include, but are not limited to, umbelliferone, fluorescein, fluorescein isothiocyanate, rhodamine, dichlorotriazinylamine fluorescein, dansyl chloride and phycoerythrin. Appropriate luminescent materials include luminol, and suitable radioactive material include radioactive phosphorous $^{32}$P, iodine I$^{125}$, I$^{131}$ or tritium.

Alternatively, the invention pertains to a method of identifying a tyrosine phosphorylated protein which is a substrate of a PTP, comprising combining a PTP of interest in which the invariant aspartate residue is replaced with an amino acid which does not cause significant alteration of the Km of the enzyme but which results in a reduction in Kcat to less than 1 per minute (less than 1 min$^{-1}$) (e.g., an alanine residue), with at least one tyrosine phosphorylated protein, thereby producing a combination; and determining the presence or absence of a complex in the combination, wherein presence of a complex in the combination between a tyrosine phosphorylated protein and the PTP indicates that the tyrosine phosphorylated protein is a substrate of the PTP.

The substrate trapping PTPs of the present invention can also be used in place of wild type PTPs to screen phosphotyrosyl peptide libraries for peptides which bind to the PTP as described in Songyang et al. (*Nature* 373:536–539 (1995); *Cell* 72:767–778 (1993)). Peptides identified from such peptide libraries can then be assessed to determine whether tyrosine phosphorylated proteins containing these peptides exist in nature.

Any tyrosine phosphorylated protein is suitable as a potential substrate in the present invention. Tyrosine phosphorylated proteins are well known in the art. Specific examples of appropriate substrates include, without limitation, p130$^{cas}$, the EGF receptor, p210 bcr:abl, MAP kinase and the insulin receptor. Of particular interest are tyrosine phosphorylated proteins which have been implicated in a mammalian disease or disorder.

The invention also pertains to a method of reducing the activity of a tyrosine phosphorylated protein, comprising administering to a mammal a PTP in which the invariant aspartate residue is replaced with an amino acid which does not cause significant alteration of the Km of the enzyme but which results in a reduction in Kcat to less than 1 per minute (less than 1 min$^{-1}$) (e.g., an alanine residue) and which forms a complex with the tyrosine phosphorylated protein. The PTP DA mutant binds to the phosphorylated protein without dephosphorylating it (or causing dephsophorylation at a greatly reduced rate), thereby inhibiting the activity of the protein and reducing its downstream effects. As used herein, "reducing" includes both reduction and complete abolishment, e.g., of one or more activities or functions of the phosphorylated protein.

For example, the invention relates to a method of reducing the transforming effects of oncogenes associated with p130$^{cas}$, a substrate of PTP-PEST, comprising administering to a mammal wild type PTP-PEST or PTP-PEST in which the invariant aspartate residue is replaced with an alanine residue. Wild type PTP-PEST binds and dephosphorylates p130$^{cas}$, thereby negatively regulating its downstream effects. DA mutants of PTP-PEST bind but do not dephosphorylate p130$^{cas}$ (or do so at a greatly reduced rate); the substrate is thus tied up in the complex with the substrate trapping form of PTP-PEST and cannot exert its downstream effects. Similarly, the invention relates to a method of reducing the formation of signalling complexes associated with p130$^{cas}$, particularly those signalling complexes which induce mitogenic pathways, comprising administering to a mammal wild type PTP-PEST or PTP-PEST in which the invariant aspartate residue is replaced with an alanine residue. The PTP binds to and/or dephosphorylates p130$^{cas}$, thereby negatively regulating the downstream effects of p130$^{cas}$ and reducing the formation of signalling complexes associated with p130$^{cas}$.

The substrate trapping mutant PTPs of the present invention can be used in virtually any application in place of, or in addition to, a corresponding wild type PTP. The advantages of such a utility lie in the ability of the mutant PTP to mimic the function of the wild type enzyme, e.g., to decrease the activity of its tyrosine phosphorylated substrate, without inducing the harmful cytotoxic effects commonly observed with administration or overexpression of the wild type PTP. Thus, the invention also pertains to a method of reducing the cytotoxic effects associated with administration or overexpression of wild type PTPs. For example, CS mutants of MKP-1 have been shown to have the same functional effect as wild type MKP-1 without induction of potentially harmful side effects. Thus, PTPs described herein, in which the invariant aspartate residue is replaced with an amino acid which does not cause significant alteration of the Km of the enzyme but which results in a reduction in Kcat to less than 1 per minute (less than 1 min$^{-1}$) (e.g., an alanine residue), can be used in many applications in place of the corresponding wild type enzyme. As used herein, a "corresponding" enzyme is one which is the same as the mutant PTP (e.g., PTP-PEST and PTP-PEST D199A) or one which is different from the mutant PTP but recognizes the same substrate as the mutant PTP.

The mutant PTPs described herein can also be used therapeutically to reduce the activity of a tyrosine phosphorylated protein, such as by a gene therapy method in which the mutant PTP described herein, or a functional portion thereof which retains the ability to bind to its tyrosine phosphorylated substrate, is introduced into a subject and in whom the mutant PTP is expressed. The mutant PTP replaces, either partially or totally, the wild type enzyme which is normally produced or competes with the wild type PTP for binding to the substrate. For example, a specific tyrosine phosphorylated protein can be identified which is implicated in a particular disease or disorder (such as a protein tyrosine kinase). At least one PTP which acts to dephosphorylate the selected tyrosine phosphorylated protein of the present invention can be identified by the methods described herein. The wild type or mutant form of the PTP can be administered to a subject in need of treatment in order to tie up or bind the tyrosine phosphorylated substrate, thereby inhibiting or reducing the function of the phosphorylated protein. In a preferred embodiment, the mutant PTP is administered in place of the wild type enzyme in order to reduce the cytotoxic effects associated with overexpression of the wild type enzyme. Procedures for gene therapy are known in the art (see U.S. Pat. No. 5,399,346 to Anderson et al.) and can be modified by methods known in the art to appropriately express the specific mutant and wild type PTPs of the present invention.

The present invention also relates to assays for identifying agents which alter, e.g., enhance or inhibit, the interaction between a PTP and its phosphorylated substrate. Agents identified by these assays can be agonists (e.g., agents which enhance or increase the activity of the PTP) or antagonists (e.g., agents which inhibit or decrease the activity of the PTP) of PTP activity. The agent may be an endogenous physiological substance or may be a natural or synthetic drug, including small organic molecules.

For example, the tyrosine phosphorylated substrate of a PTP can be identified by the methods described herein. An enzymatic activity assay utilizing the wild type PTP can be carried out in the presence of an agent to be tested, and the resulting amount of enzyme activity can be compared with the amount of enzyme activity in the absence of the agent to be tested. Enzymatic activity assays are known in the art; for example, assays of PTP activity using a tyrosine phosphorylated $^{32}$P-labelled substrate are described in Flint et al. (*EMBO J.* 12:1937–1946 (1993)). A decrease in the enzymatic activity in the presence of the agent to be tested indicates that the agent inhibits the interaction between the PTP and its substrate. Conversely, an increase in the enzymatic activity in the presence of the agent to be tested indicates that the agent enhances the interaction between the PTP and its substrate.

Alternatively, a competitive binding assay can be carried out utilizing the mutant PTP in the presence of an agent to be tested, and the resulting extent of binding of the mutant PTP to its substrate can be compared with the extent of binding in the absence of the agent to be tested. Competitive binding assays are known in the art; for example, U.S. Pat. No. 5,352,660 to Pawson describes methods suitable for use in this invention. A decrease in the extent of binding in the presence of the agent to be tested indicates that the agent inhibits the interaction between the PTP and its substrate. Conversely, an increase in the extent of binding in the presence of the agent to be tested indicates that the agent enhances the interaction between the PTP and its substrate.

According to the present invention, tyrosine phosphorylated peptides identified with mutant PTPs from peptide libraries by the methods of Songyang et al. (*Nature* 373:536–539 (1995); *Cell* 72:767–778 (1993)) can be used herein in place of the complete tyrosine phosphorylated protein in competitive binding assays.

The present invention also pertains to pharmaceutical compositions comprising a PTP in which the invariant aspartate residue is replaced with an amino acid which does not cause significant alteration of the Km of the enzyme but which results in a reduction in Kcat to less than 1 per minute (less than 1 min$^{-1}$) (e.g., an alanine residue). For instance, the PTP of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known to medicinal chemists, and will depend on the ultimate pharmaceutical formulation desired. Methods of introduction of exogenous PTPs at the site of treatment include, but are not limited to, intradermal, intramuscular, intraperitoneal, intravenous, subcutaneous, oral and intranasal. Other suitable methods of introduction can also include rechargeable or biodegradable devices and slow release polymeric devices. The pharmaceutical compositions of this invention can also be administered as part of a combinatorial therapy with other agents.

The following Examples are offered for the purpose of illustrating the present invention and are not to be construed to limit the scope of this invention. The teachings of all references cited herein are hereby incorporated by reference in their entirety.

EXAMPLES

Materials and Methods

The following is a description of the materials and methods used in the work described herein.

Generation, Expression and Purification of Mutant PTP Proteins

Point mutations within the catalytic domains of PTP-PEST (D 199A, C231S) and PTP1B (D181A, C215S) were introduced by site-directed mutagenesis using the Muta-Gene™ in vitro mutagenesis kit (Bio-Rad, Richmond, Calif.). Regions containing the required point mutation were then exchanged with the wild type sequences within appropriate expression vectors, and the replaced mutant regions were sequenced in their entirety to verify the absence of additional mutations.

Full length PTP-PEST proteins (wild type and mutant proteins, containing either Asp199 to Ala or Cys231 to Ser mutations) and the wild type PTP-PEST catalytic domain (amino acids 1–305) were expressed in Sf9 cells using recombinant baculovirus (BaculoGold™, Pharmingen, San Diego, Calif.), and purified as described in Garton and Tonks (*EMBO J.* 13:3763–3771 (1994)). Truncated forms of wild type and mutant PTP-PEST proteins, comprising amino acid residues 1–305 of PTP-PEST were also expressed in *E. coli* as GST fusion proteins following subcloning of PTP-PEST DNA in-frame downstream of GST in pGEX vectors (Pharnacia Biotech Inc., Uppsala, Sweden). Twenty-five ml of *E. coli* transformed with the appropriate vector were grown to log phase (OD$_{600}$ approximately 0.5). Fusion protein expression was then induced by addition of 0.2 mM isopropyl-1-thio-b-D-galactopyranoside, and the cells were grown for 2-4 hours at 30° C. Cells were harvested by centrifugation, incubated with 50 mg/ml lysozyme in 3 ml buffer containing 50 mM Tris-HCl, pH 7.4, 5mM EDTA, 1 mM PMSF, 1 mM benzamidine, 5 mg/ml leupeptin, 5 mg/ml aprotinin, 0.1% Triton X-100 and 150 mM NaCl, then lysed by sonication (3×10s). Following removal of insoluble material by centrifugation (20 minutes at 300,000×g), fusion proteins were isolated by incubation for 30 min at 4° C. with 100 ml glutathione-Sepharose beads (Pharmacia Biotech Inc., Uppsala, Sweden), and the beads were then collected by centrifugation and washed three times with buffer A (20 mM Tris-HCl, pH 7.4, 1 mM EDTA, 1 mM benzamidine, 1 mg/ml leupeptin, 1 mg/ml aprotinin, 10% glycerol, 1% Triton X-100 and 100 mM NaCl). This procedure yielded essentially homogeneous fusion protein at a concentration of 1 mg protein/ml glutathione-Sepharose beads. PTP1B proteins (wild type and mutant forms) comprising amino acids 1–321 were expressed in E.coli and purified to homogeneity as described in Barford et al. (J. Mol. Biol. 239:726–730 (1994)).

Cell Culture, Transfection, Preparation of Lysates and Fractionation

HeLa and COS cells were grown in Dulbecco's modified Eagle's medium (DMEM), containing 5% fetal bovine serum (FBS); Wi38, C2C12 and MvLu cells were grown in DMEM containing 10% FBS; 293 cells were grown in DMEM containing 10% calf serum; MCF10A cells were grown in 50% DMEM, 50% Ham's F-12 containing 5% horse serum, 20 ng/ml epidermal growth factor, 10 mg/ml insulin, 0.5 mg/ml hydrocortisone and 0.25 mg/ml fungizone. All media also contained penicillin and streptomycin at 100 U/ml and 100 mg/ml, respectively, and all cells were grown at 37° C. Calcium phosphate-mediated transfection was used to introduce cDNA encoding wild type and mutant PTP-PEST proteins into COS cells. These were encoded by PTP-PEST cDNA subcloned into the plasmid PMT2, from which expression was driven by an adenovirus major late promoter; 20 mg DNA was used for transfection of each 10 cm plate of cells. The level of expression of PTP-PEST constructs was similar in all cases.

Prior to cell lysis, 70–90% confluent cultures of cells were treated for 30 minutes with 0.1 mM pervanadate (20 ml of a fresh solution containing 50 mM sodium metavanadate ($NaVO_3$) and 50 mM $H_2O_2$ were added to 10 ml medium). Treatment of cells with $H_2O_2$ and vanadate leads to a synergistic increase in phosphotyrosine levels, presumably due to inhibition of intracellular PTPs by vanadate. The synergism between $H_2O_2$ and vanadate has previously been suggested to result from improved accumulation of the resultant oxidized vanadate (pervanadate) within the cells when compared to vanadate itself (Heffetz et al., J. Biol. Chem. 265:2896–2902 (1990)). It is important to note that during the preparation of cell lysates, dilution occurs such that the inhibitory effect of vanadate on PTP action is lost. Pervanadate treatment resulted in the appearance of at least 50 prominent phosphotyrosine protein bands in all cell types, whereas untreated cells contained virtually undetectable levels of phosphotyrosine (data not shown).

Cells were lysed in Buffer A containing 5 mM iodoacetic acid, which was included in order to inhibit irreversibly cellular PTPs. Following incubation at 4° C. for 30 minutes, 10 mM DTT was added to inactivate any unreacted iodoacetic acid. Insoluble material was then removed by centrifugation for 20 minutes at 300,000×g. The resultant lysates were stable with regard to their phosphotyrosine content during long term (several months) storage at -70° C. and during prolonged (at least 20 hours) incubation at 4° C., in the absence of exogenous added PTPs.

Pervanadate-treated HeLa cell lysate was fractionated by anion exchange chromatography using a Mono Q FPLC column (Pharmacia). The sample (50 mg total protein at 3 mg/ml in buffer A) was diluted in three volumes of buffer B (20 mM tris-HCl, pH 7.4, 1 mM EDTA, 1 mM benzamidine, 1 mg/ml leupeptin, 1 mg/ml aprotinin and 0.1% Triton X-100) prior to loading. Proteins were eluted at a flow rate of 1 ml/min with a linear gradient of 0–0.5 M NaCl in buffer B over 20 fractions (1 ml fraction volume), followed by a second gradient of 0.5–1.0 M NaCl in buffer B over 5 fractions. Phosphotyrosine-containing proteins were detected within fractions 7–21 according to anti-phosphotyrosine immunoblotting. The same procedures were followed for PTP1B, with the exception that the cells were not treated with pervanadate.

Dephosphorylation Reactions

Lysates of pervanadate-treated HeLa cells (1–2 mg protein/ml) containing tyrosine phosphorylated proteins were incubated on ice in the absence or presence of purified active PTPs at a concentration of 2 nM. Dephosphorylation was terminated by the removal of aliquots (30 mg protein) into SDS-PAGE sample buffer, and the extent of dephosphorylation was determined by immunoblotting using the monoclonal antibody G104. Assays of PTP activity using tyrosine phosphorylated $^{32}$P-labelled RCM-lysozyme as substrate were performed as described in Flint et al. (EMBO J. 12:1937–1946 (1993)).

Antibodies and Immunoblotting

The PTP-PEST monoclonal antibody AG25 was raised against baculovirus-expressed purified full-length PTP-PEST. The anti-phosphotyrosine monoclonal antibody G104 was generated using as antigen phosphotyrosine, alanine and glycine, in a 1:1:1 ratio, polymerized in the presence of keyhole limpet hemocyanin with 1-ethyl-3-(3'-dimethylaminopropyl)carbodiimide, a method originally described in Kamps and Sefton (Oncogene 2:305–315 (1988)). p130$^{cas}$ monoclonal antibody was from Transduction Laboratories (Lexington, Ky.). Monoclonal antibody FG6 against PTP1B was provided by Dr David Hill (Calbiochem Oncogene Research Products, Cambridge, Mass.). Visualization of proteins by immunoblotting was achieved by enhanced chemiluminescence (ECL) using HRP-conjugated secondary antibodies (Amersham Life Science Inc., Arlington Heights, Ill.) and the SuperSignal™ CL-HRP substrate system (Pierce, Rockford, Ill.).

Immunoprecipitation and Substrate Trapping

Immunoprecipitation of PTP-PEST from transfected COS cells was performed following covalent coupling of monoclonal antibody AG25 to protein A-Sepharose beads (Pharmacia Biotech Inc., Uppsala, Sweden) using the chemical cross-linking agent dimethyl pimelimidate (Schneider et al., J. Biol. Chem. 257:10766–10769 (1982)). Antibody was first bound to protein A-Sepharose at a concentration of 1 mg/ml bead volume, and unbound material was then removed by three washes with 0.2 M sodium borate, pH 9. Covalent coupling was achieved by incubation at room temperature for 30 minutes in the presence of 20 mM dimethyl pimelimidate in 0.2 M sodium borate, pH 9. The beads were then incubated for 1 hour with an excess of 0.2 M ethanolamine, pH 8, to block any unreacted cross-linker, and washed three times with PBS prior to storage at 4° C. Ten ml of AG25 beads were used to precipitate transfected PTP-PEST from lysates containing approximately 0.375 mg protein.

Substrate trapping was performed using various PTP affinity matrices. The full-length PTP-PEST matrix utilized covalent coupled AG25-protein A-Sepharose beads to which purified baculovirus-expressed PTP-PEST protein was bound. Aliquots (10 ml) of AG25 beads were incubated for 2 hours at 4° C. in 100 ml buffer A in the presence of 5 mg of purified PTP-PEST (wild type or mutant forms); unbound PTP-PEST was then removed by washing three times with 1 ml buffer A. The resultant PTP-PEST-AG25-protein A-Sepharose beads contained approximately 2 mg of PTP-PEST per 10 ml aliquot. Substrate trapping was also carried out with glutathione-Sepharose beads bound to bacterially-expressed GST fusion proteins containing the catalytic domain of PTP-PEST.

PTP1B was also used in substrate trapping experiments. In this case, the monoclonal antibody FG6 was precoupled to protein A-Sepharose in the absence of cross-linker (2 mg antibody/10 ml beads), then purified PTP1B proteins were added in excess and incubated at 4° C. for 2 hours. Following removal of unbound PTP1B, 10 ml beads contained approximately 2 mg PTP1B.

Pervanadate-treated cell lysates, or column fractions, were used as a source of phosphotyrosine-containing proteins for substrate trapping experiments. In general, lysates containing 0.25–0.5 mg protein in 0.5 ml buffer A (including 5 mM iodoacetic acid, 10 mM DTT) were incubated at 4° C. for 2 hours in the presence of 10 ml of affinity matrix containing approximately 2 mg of the appropriate PTP protein. Unbound proteins were then removed from the samples by washing three times with 1 ml buffer A, and bound material was collected by addition of 50 ml SDS-PAGE sample buffer followed by heating at 95° C. for 5 minutes; proteins bound to the beads were then analyzed by SDS-PAGE followed by immunoblotting.

Results

The following details the results of the work described herein carried out as described above.

PTP1B and p210bcr:abl

Chronic myelogenous leukemia (CML) is a clonal disorder of the haematopoietic stem cell that is characterized by the Philadelphia chromosome, in which the c-Abl proto-oncogene on chromosome 9, encoding a PTK, becomes linked to the bcr gene on chromosome 22. This results in the generation of a bcr:able fusion protein, p210 bcr:abl, in which the PTK activity is enhanced relative to that of c-Abl. Current data indicates that this cytogenetic abnormality is the primary and sole causative event in CML. Expression of p210 bcr:abl produces abnormal patterns of tyro sine phosphorylation that result in the aberrant maturation of the haematopoietic stem cell that is characteristic of CML.

Expression of PTP1B mRNA and protein is enhanced as a consequence of p210 bcr:abl expression in Rat1, Mo7 and BaF3 cells. Changes in PTP1B activity, which were commensurate with the change in enzyme protein, were also observed. These changes are specific for PTP1B and are not seen in closely related homologue (65% identity) TC-PTP or in other tested PTPs, including SHP-1, SHP-2 and PTP-PEST. The increase in expression of PTPIB was also observed in Ph+B-lymphoid cells derived from a CML patient relative to Ph– cells from the same patient.

The changes in PTP1B levels were induced specifically by p210 bcr:abl and were not seen in cells expressing other PTKs including v-abl, v-src or other oncoproteins such as myc. The PTK activity of p210bcr:abl was essential for the increase in expression of PTP1B, since expression of an inactive lysine to arginine mutant form of p210 bcr:abl in Rat1 cells did not alter PTP1B levels. The increase in PTP1B levels is a rapid response to induction of p210 bcr:abl. When BaF3 cells expressing a temperature-sensitive mutant form of p210 bcr:abl were shifted to the permissive temperature for the PTK, PTP1B levels were observed to increase within 12–24 hours coincident with the appearance of the active form of the PTK. These data indicate that the alteration in PTP1B levels is a relatively rapid response to the appearance of p210 bcr:abl, rather than a long-term adaptive response of the cells.

In transient cotransfection experiments in COS cells, PTP1B dephosphorylates p210 bcr:abl but not v-abl. When the PTP1B D181A mutant was expressed as a GST fusion protein, purified and incubated with lysates of Mo7-p210 cells (which overexpress p210 bcr:abl), a complex of the mutant PTP and p210 bcr:abl was isolated. In contrast, tyrosine phosphorylated c-abl, which was also present in the lysates, did not bind to the mutant PTP. The interaction between PTP1B D181A and p210 bcr:abl was blocked by vanadate, suggesting that the interaction involved the active site of the PTP.

Following transient coexpression in COS cells, PTP1B D181A formed a complex with p210 bcr:abl. Preliminary data indicate that the Y177F mutant form of p210 bcr:abl did not interact with PTP1b D181A, suggesting that this tyrosine residue is a component of the binding site in the PTK. This tyrosine residue in p210 bcr:abl is phosphorylated in vivo and has been demonstrated to serve as a docking site for GRB2. Direct interaction of the pTyr in p210 bcr:abl and the SH2 domain of GRB2 is essential for the transforming activity of the PTK. Interaction of PTP1B D181 A with p210 bcr:abl interferes with the association of the PTK with GRB2. Taken together, these data suggest that p210 bcr:abl is a physiological substrate of PTP1B and that PTP1B may function as an antagonist of the oncoprotein PTK in vivo. The Vmax, Km and Kcat of 37 kDa PTP1B mutants toward RCML are shown in FIG. 2.

PTP1B and the EGF Receptor

Expression of PTP1B D181A in COS cells leads to enhanced phosphorylation of tyrosyl residues in a 180 kDa protein and in proteins of 120 and 70 kDa. When a GST-PTP1B D181A fusion protein is expressed in COS cells and precipitated on Glutathione-Sepharose, the 180 kDa, and smaller quantities of p120 nd p70, were coprecipitated. The p180 protein was identified as the epidermal growth factor (EGF) receptor by immunoblotting. The identity of the p120 and p70 proteins is unclear; however, the latter is not src, p62 or paxillin.

Expression of PTP1B D181A in COS cells induces tyrosine phosphorylation of the EGF receptor in the absence of its ligand, EGF, indicating that the mutant PTP is exerting its effects in the intact cell and not post-lysis. The equivalent D199A PTP-PEST mutant does not interact with the EGF receptor, indicating the specificity of this substrate interaction.

Autophosphorylation of the EGF receptor is required for the interaction with PTP1B D181A. Mutants of the receptor that are either kinase-dead or in which the autophosphorylation sites have been deleted do not interact with PTP1B D181A. In v-src-expressing cells, a plethora of tyrosine phosphorylated proteins were observed, but phosphorylation of the EGF receptor was not detected. Under these conditions, PTP1B D181A bound predominantly to a 70 kDa tyrosine phosphorylated protein.

As a result of this work, it appears that PTP 1B can modulate EGF-induced signalling pathways, perhaps including the pathways of many diseases, including breast cancer.

Preferential Dephosphorylation of a 130 kDa Phosphotyrosine-Containing Protein by PTP-PEST In order to investigate the substrate specificity of PTP-PEST in vitro, aliquots of pervanadate-treated HeLa cell lysates were incubated on ice, yielding 50–100 distinct phosphotyrosine-containing proteins as judged by immunoblotting of the cell lysate using the monoclonal anti-phosphotyrosine antibody G104. Purified full-length PTP-PEST (expressed in Sf9 cells using recombinant baculovirus), PTP-PEST catalytic domain, or PTP1B catalytic domain (37 kDa form) was then added to the lysate, and aliquots were removed at various time points for analysis by SDS-PAGE followed by anti-phosphotyrosine immunoblotting.

Surprisingly, a prominent 130 kDa phosphotyrosine band (p130) was selectively dephosphorylated by PTP-PEST within 10 minutes, whereas the intensity of all the other bands was essentially unchanged even after 60 minutes of incubation with PTP-PEST. Long incubations with higher concentrations of PTP-PEST (greater than 100-fold) resulted in the complete removal of all phosphotyrosine bands from the lysate. However, under all conditions tested, p130 was found to be dephosphorylated more rapidly than all other bands present.

The selective dephosphorylation of p130 by PTP-PEST was also observed using a truncated form of the phosphatase (amino acid residues 1–305) which essentially contains only the catalytic domain of the enzyme. This result suggests that the striking substrate preference displayed by PTP-PEST in this analysis is an inherent property of the phosphatase catalytic domain, whereas the C-terminal 500 amino acid residues have little discernible effect on the substrate specificity of the enzyme.

The specificity of the interaction between PTP-PEST and p130 was addressed using the catalytic domain of PTP1B (amino acid residues 1–321) in dephosphorylation reactions. When added at a similar molar concentration to that used for PTP-PEST, PTP1B was found to dephosphorylate fully and rapidly (within 15 minutes) most of the phosphotyrosine-containing proteins present in the pervanadate-treated HeLa lysate. In addition, the time course of dephosphorylation of p130 was not significantly more rapid than that of the other phosphotyrosine bands dephosphorylated by PTP1B. It should be noted, however, that these in vitro dephosphorylation results are not truly illustrative of the substrate specificity of PTP1B in vivo for several reasons. First, only the isolated catalytic subunit was used in this particular experiment. Furthermore, in vivo substrate specificity may be quite different due to the intracellular distribution of both the PTP and potential substrates. That is, in vitro dephosphorylation experiments may utilize substrates which the PTP is capable of dephosphorylating but which it would not have access to in vivo. The phenomenon of differing substrate specificity depending upon different physiologic contexts is illustrated by a comparison of this data with the in vivo PTP1B work described above, wherein PTP1B showed specificity for only three proteins.

Identification of Phosphotyrosine-Containing p130 Protein as p130$^{cas}$ by Substrate Trapping Pervanadate-treated HeLa cell lysate was fractionated by anion exchange chromatography and aliquots of the fractions were analyzed by SDS-PAGE followed by immunoblotting with anti-phosphotyrosine or anti-p130$^{cas}$ antibodies. Aliquots of all samples analyzed were then incubated with an affinity matrix containing a substrate trapping PTP-PEST mutant, comprising full length PTP-PEST in which Asp199 is changed to alanine (D199A), bound to covalently coupled protein A-Sepharose/antibody (AG25) beads. Proteins associated with PTP-PEST were then analyzed by SDS-PAGE followed by immunoblotting with anti-phosphotyrosine or anti-p130$^{cas}$ antibodies.

Anti-phosphotyrosine immunoblotting of the column fractions showed that the p130 phosphotyrosine band eluted as a single peak in fractions 11–14 (approx. 0.3 M NaCl). In view of the abundance of tyrosine phosphorylated p130 in HeLa lysates, it appeared likely that p130 represents a previously identified phosphotyrosine-containing 130 kDa protein. Several potential candidates were identified in the literature, including the focal adhesion kinase p125$^{FAK}$, ras-GAP, gp130 and p130$^{cas}$. Of these candidates, p130$^{cas}$ has been identified as a particularly prominent phosphotyrosine band in a wide variety of systems, including v-crk (Mayer and Hanafusa, Proc. Natl. Acad. Sci. USA 87: 2638–2642 (1990); Mayer et al., Nature 332:272–275 (1988)) and src (Kanner et al., Proc. Natl. Acad. Sci. USA 87:3328–3332 (1990); Reynolds et al., Mol. Cell. Biol. 9: 3951–3958 (1989)) transformed fibroblasts, integrin-mediated cell adhesion (Nojima et al., J. Biol. Chem. 270:15398–15402 (1995); Petch et al., J. Cell Science 108:1371–1379 (1995); Vuori and Ruoslahti, J. Biol. Chem. 270:22259–22262 (1995)) and PDGF stimulated 3T3 cells (Rankin and Rozengurt, J. Biol. Chem. 269:704–710 (1994)).

Therefore, the possibility that the p130 phosphotyrosine band corresponds to p130$^{cas}$ was tested by immunoblotting the Mono Q fractions using an antibody to p130$^{cas}$. The 130 kDa band corresponding to p130$^{cas}$ eluted in the same fractions as the p130 tyrosine phosphorylated band, and displayed a similar apparent molecular weight, suggesting that they might represent the same protein. Furthermore, p130$^{cas}$ immunoprecipitated from these fractions was found to be phosphorylated on tyrosyl residues.

A mutant form of PTP-PEST (D199A) was generated by site-directed mutagenesis, and the mutant enzyme was purified following expression using recombinant baculovirus. When assayed using tyrosine phosphorylated RCM-Lysozyme as substrate, the purified mutant enzyme exhibited a specific activity which was approximately 10,000 fold lower than that of the wild type enzyme (Garton and Tonks, unpublished data). This purified protein was bound to an affinity matrix comprised of an anti-PTP-PEST monoclonal antibody (AG25) covalently coupled to Protein A-Sepharose beads, then incubated with each of the Mono Q fractions. After 45 minutes of incubation, proteins associating with the mutant PTP-PEST were collected by centrifugation, the beads were washed, and SDS-PAGE sample buffer was added. Associated proteins were then analyzed by immunoblotting using the monoclonal anti-phosphotyrosine antibody G104.

The mutant PTP-PEST protein was found to associate with a single phosphotyrosine-containing protein, the molecular weight (130 kDa) and Mono Q elution position (fractions 11–14) of which coincided with those of p130$^{cas}$. Immunoblotting of the PTP-PEST-associated proteins using the p130$^{cas}$ antibody demonstrated that the 130 kDa tyrosine phosphorylated protein trapped by the mutant PTP-PEST is indeed p130$^{cas}$. These data further support the hypothesis that p130$^{cas}$ is a potential physiologically relevant substrate for PTP-PEST.

Determination of Structural Features of PTP-PFST Involved in Specific Interaction with Tyrosine Phosphorylated p130$^{cas}$ The interaction between p130$^{cas}$ and PTP-PEST was investigated further in substrate trapping experiments using various purified mutant forms of PTP-PEST to precipitate proteins from pervanadate-treated HeLa lysates. Several affinity matrices were incubated with pervanadate-treated HeLa cell lysate, and proteins associated with the beads were analyzed by SDS-PAGE followed by immunoblotting with anti-phosphotyrosine or anti-p130$^{cas}$ antibodies.

The wild type full-length phosphatase was found to be incapable of stable association with tyrosine phosphorylated p130$^{cas}$, whereas both the PTP-PEST (D199A) mutant protein and a mutant lacking the active site cysteine residue (C231S) specifically precipitated p130$^{cas}$ from the lysate. The inability of the wild type phosphatase to precipitate tyrosine phosphorylated p130$^{cas}$ presumably reflects the transient nature of the normal interaction between PTP-PEST and tyrosine phosphorylated p130$^{cas}$, which is likely to be concluded as soon as p130$^{cas}$ is dephosphorylated by PTP-PEST.

Since the C-terminal 500 amino acids of PTP-PEST contain several proline-rich regions which resemble src homology-3 (SH3) domain binding sequences, it appeared plausible that the specificity of the interaction between PTP-PEST and p130$^{cas}$ might depend to some extent on association of these segments with the SH3 domain of p130$^{cas}$. The possible contribution of the C-terminal segment of PTP-PEST in the observed specific interaction of PTP-PEST with p130$^{cas}$ was therefore addressed in further substrate trapping experiments using GST fusion proteins containing the catalytic domain of PTP-PEST alone, in both wild type and mutant (D199A) forms. The mutant catalytic domain of PTP-PEST fused to GST was found to precipitate the p130$^{cas}$ phosphotyrosine band specifically, whereas both the wild type fusion protein and GST alone failed to precipitate p130$^{cas}$. The specific interaction between PTP-PEST and p130$^{cas}$ observed in these experiments therefore appears to be an intrinsic property of the catalytic domain of PTP-PEST, emulating the observed preference of the active PTP-PEST catalytic domain for dephosphorylation of p130$^{cas}$ in vitro.

Specificity of Interaction Between Mutant PTP-PEST and Tyrosine Phosphorylated p130$^{cas}$ In view of the relative abundance of tyrosine phosphorylated p130$^{cas}$ in the pervanadate-treated HeLa cell lysate, the possibility that the observed selective binding of PTP-PEST inactive mutant proteins to p130$^{cas}$ was substrate-directed (reflecting the abundance of this potential substrate relative to the other phosphotyrosine-containing proteins present in the lysate) rather than enzyme-directed (reflecting a genuine substrate preference of PTP-PEST) was considered; this possibility was addressed in two ways. First, inactive mutant forms of the catalytic domain of PTP1B were used to trap potential substrates for this enzyme from the pervanadate-treated HeLa lysates. Again it was found that the wild type phosphatase was incapable of stable interaction with any phosphotyrosine-containing protein, whereas mutant variants of the PTP1B phosphatase domain (comprising Cys or Asp mutations analogous to those described above for PTP-PEST) associated with many tyrosine phosphorylated proteins. This was especially apparent for the aspartic acid mutant of PTP1B (D181A), which appeared to precipitate essentially all phosphotyrosine-containing proteins from the lysate with similar efficacy. These data emphasize the specific nature of the interaction between PTP-PEST and p130$^{cas}$, which appears to be a property peculiar to the PTP-PEST catalytic domain, rather than a feature shared by all PTP catalytic domains.

The specificity of the interaction between PTP-PEST and p130$^{cas}$ was addressed further following pervanadate-treatment of several different cell lines (Wi38, 293, COS, MCF10A, C2C12, MvLu), yielding a different array of tyrosine phosphorylated proteins in each case; the resultant lysates were analyzed by SDS-PAGE followed by anti-phosphotyrosine immunoblotting. Aliquots were incubated with PTP-PEST (D199A) affinity matrix or control matrix, and tyrosine phosphorylated proteins associating with PTP-PEST were analyzed by SDS-PAGE and immunoblotting with anti-phosphotyrosine or anti-p130$^{cas}$ antibodies as described above.

In each case, the D199A mutant PTP-PEST protein precipitated a single broad phosphotyrosine band with an apparent molecular weight between 120 and 150 kDa in different cell lines, whereas the affinity matrix alone failed to precipitate any phosphotyrosine-containing protein. Immunoblotting of the precipitates with a p130$^{cas}$ antibody revealed that the protein precipitated from all cell lysates corresponded to p130$^{cas}$; the observed molecular weight variation between different cell lines presumably reflects either species differences in the molecular weight of p130$^{cas}$ or expression of different alternatively spliced forms (Sakai et al., EMBO J. 13:3748–3756 (1994)).

The relative abundance of tyrosine phosphorylated p130$^{cas}$ in the PTP-PEST precipitates appeared to correlate approximately with the abundance of p130$^{cas}$ protein in the lysates (data not shown). Surprisingly, regardless of the abundance of tyrosine phosphorylated p130$^{cas}$ in the lysates, p130$^{cas}$ was invariably the only phosphotyrosine-containing protein in the precipitates, even in 293 cell lysates which contained very little p130$^{cas}$ protein but which displayed a wide variety of other abundantly tyrosine phosphorylated proteins. Similarly, when lysates of pervanadate-treated 293 cells (containing tyrosine phosphorylated p130$^{cas}$ in amounts which are undetectable by anti-phosphotyrosine immunoblotting of the lysate) were incubated with active PTP-PEST, no visible dephosphorylation of any phosphotyrosine band occurred (Garton and Tonks, unpublished data). These results indicate that the affinity of PTP-PEST for p130$^{cas}$ is substantially greater than for any other substrate present, and further emphasizes the remarkable substrate selectivity of PTP-PEST for p 130$^{cas}$.

Vanadate Inhibition of Tyrosine Phosphorylated p130$^{cas}$ Association with Mutant PTP-PEST A consistent observation of this work was that, in contrast to the inactive mutant PTP-PEST, the wild type enzyme failed to associate in a stable complex with tyrosine phosphorylated p130$^{cas}$, suggesting that the observed association is active site-directed. In order to investigate this possibility, mutant PTP-PEST (D199A) was incubated with the PTP inhibitor vanadate at various concentrations prior to addition of pervanadate-treated HeLa cell lysate. The extent of association of p130$^{cas}$ with PTP-PEST was then analyzed. PTP-PEST affinity matrix, comprising full length PTP-PEST (D199A) bound to covalently coupled protein A-Sepharose/antibody (AG25) beads, was incubated for 10 minutes on ice in the presence of varying concentrations of sodium orthovanadate. The samples were then incubated with aliquots of pervanadate-treated HeLa cell lysate; associated proteins were analyzed by SDS-PAGE and immunoblotting with anti-phosphotyrosine or anti-p130$^{cas}$ antibodies. The activity of wild type PTP-PEST was also determined under the same conditions, using tyrosine phosphorylated $^{32}$P-labelled RCM-lysozyme as substrate.

The association was found to be potently disrupted by vanadate, with a concentration-dependence similar to that of vanadate inhibition of wild type PTP-PEST, and complete disruption being observed at 10 mM vanadate. Since PTP inhibition by vanadate presumably results from a direct interaction of vanadate with the active site cysteine residue of the enzyme (Denu et al., Proc. Natl. Acad. Sci. USA 93:2493–2498 (1996)), this result supports the hypothesis that the stable association of mutant PTP-PEST with tyrosine phosphorylated p130$^{cas}$ is mediated by direct interactions between active site residues within PTP-PEST, in particular the active site cysteine residue, and phosphotyrosine moieties within p130$^{cas}$.

Association of Endogenous p130$^{cas}$ with Transfected Mutant PTP-PEST in COS Cells The work described above strongly suggests that p130$^{cas}$ represents a potential physiologically significant substrate for PTP-PEST. In order to assess whether PTP-PEST interacts with p130$^{cas}$ in intact cells, COS cells were transfected with plasmids encoding wild type or mutant forms of PTP-PEST (D199A or C215S). The cells were treated with pervanadate 30 minutes prior to lysis, PTP-PEST proteins were immunoprecipitated, and associated tyrosine phosphorylated proteins were analyzed by anti-phosphotyrosine immunoblotting of the resultant precipitates. Lysates were also incubated with covalently coupled protein A-Sepharose/anti-PTP-PEST (AG25) beads and associated proteins were analyzed by SDS-PAGE and immunoblotting with anti-phosphotyrosine antibody.

Under these conditions, the phosphotyrosine-containing band corresponding to p130$^{cas}$ was again unique in its ability to associate with the C231S PTP-PEST protein, indicating that p130$^{cas}$ can be specifically selected by PTP-PEST as a substrate in an intracellular context in the presence of a large number of alternative possible substrates. Neither the wild type nor the D199A form of PTP-PEST was capable of a stable interaction with tyrosine phosphorylated p130$^{cas}$ in pervanadate-treated COS cells.

The binding of both wild type and D199A PTP-PEST to tyrosine phosphorylated p130$^{cas}$ under these conditions is most likely prohibited by the presence of pervanadate bound to the active site cysteine residue of PTP-PEST (Denu et al., *Proc. Natl. Acad. Sci. USA* 93:2493–2498 (1996)), which effectively excludes the binding of phosphotyrosine residues of p130$^{cas}$. The ability of the C231S mutant PTP-PEST to associate in a stable complex with p130$^{cas}$ in the presence of pervanadate suggests that this mutant protein is largely unaffected by pervanadate, indicating that the normal mode of inhibition of PTPs by vanadate ions depends critically on direct interactions between vanadate and the thiolate anion of the PTP active-site cysteine residue. These observations therefore lend further support to the existence of an exclusive interaction between PTP-PEST and p130$^{cas}$ which appears to be entirely active site-directed, and therefore reflects the genuine, inherent, highly restricted substrate preference of PTP-PEST for p130$^{cas}$.

Results described herein implicate p130$^{cas}$ as a physiologically relevant substrate for PTP-PEST. Furthermore, the observed stringency and exclusivity of the interaction between PTP-PEST and p130$^{cas}$ in a wide variety of cell lines suggest that p130$^{cas}$ may be a unique high affinity substrate for PTP-PEST, although the possibility that other significant PTP-PEST substrates may exist cannot be excluded at present. In particular, it is unclear whether pervanadate-treated cells display a complete spectrum of all possible tyrosine phosphorylated proteins; in fact this appears unlikely since pervanadate treatment presumably results only in an increase in tyrosine phosphorylation of proteins which are to some extent constitutively phosphorylated, but which are normally rapidly dephosphorylated, within the cell. Potential substrates lacking from pervanadate-treated cells therefore presumably include substrates of protein tyrosine kinases (PTKs) which are normally present in an inactive state, such as ligand-stimulated receptor PTKs, and the recently described calcium regulated kinase PYK2 (Lev et al., *Nature* 376: 737–745 (1995)). Regardless of these considerations, the ability of PTP-PEST to select p130$^{cas}$ exclusively as a substrate from lysates of several different cell lines, containing a combined total of at least one hundred different potential substrates (many of which presumably contain multiple sites of phosphorylation), clearly demonstrates that the substrate specificity of PTP-PEST is highly restricted.

Many intracellular PTPs are limited in their substrate availability due to strict confinement within a particular subcellular location; examples include PTP1B, which is localized to the cytoplasmic face of the endoplasmic reticulum (Frangioni et al., *Cell* 68:545–560 (1992)), and TCPTP which is either nuclear (Tillmann et al., *Mol. Cell. Biol.* 14:3030–3040 (1994)) or localized to the endoplasmic reticulum, depending upon which alternative spliced form is expressed (Lorenzen et al., *J. Cell Biol.* 131:631–643 (1995)). Alternatively, certain PTPs appear to be highly regulated, requiring activation before appreciable activity can be demonstrated. For example, the SH2 domain-containing PTPs, SHP1 and SHP2, display relatively low activity in vitro, but can be considerably activated by several mechanisms including C-terminal truncation (Zhao et al., *J. Biol. Chem.* 268:2816–2820 (1993)), addition of certain phospholipids (Zhao et al., *Proc. Natl. Acad. Sci. USA* 90:4251–4255 (1993)), or SH2 domain-mediated binding of appropriate phosphotyrosine-containing peptides (Lechleider et al., *J. Biol. Chem.* 268:21478–21481 (1993)).

However, PTP-PEST exhibits high specific activity in vitro (35,000 U/mg), and is a predominantly (90–95%) soluble PTP within cells (Garton and Tonks, unpublished data); in principle, therefore, it may act potently on any substrate accessible to the cytoplasm. This accessibility may partly underlie the necessity for PTP-PEST to possess an inherently constrained substrate specificity. The demonstration that mutant PTP-PEST is capable of exclusively associating with p130$^{cas}$ in an intracellular context in the presence of many other tyrosine phosphorylated proteins, is an indication that the narrow substrate specificity of the enzyme may result in PTP-PEST having a negligible influence on the phosphorylation state of the majority of tyrosine phosphorylated proteins within the cell, even though those substrates are largely accessible to PTP-PEST.

The role of $p_{130}{}^{cas}$ in cellular transformation by the v-crk and v-src oncogenes is unclear, although there is a general correlation between the level of tyrosine phosphorylation of p130$^{cas}$ and the degree of transformation in cells expressing different forms of crk or src (Kanner et al., *EMBO J.* 10:1689–1698 (1991); Mayer and Hanafusa, *J. Virol.* 64:3581–3589 (1990)). Furthermore, enhanced tyrosine phosphorylation of p130cas has also been observed in cells transformed by c-Ha-ras and by ornithine decarboxylase overexpression (Auvinen et al., *Mol. Cell. Biol.* 15:6513–6525 (1995)). Expression of antisense cDNA encoding p130$^{cas}$ in these cells results in a partial reversion of the transformed phenotype. These observations suggest that aberrant tyrosine phosphorylation of $p_{130}{}^{cas}$ is a common feature of cells transformed by several disparate mechanisms and that p130$^{cas}$ may be required for full manifestation of the transformed state. Dephosphorylation of p130$^{cas}$ by PTP-PEST is therefore a potentially important regulatory mechanism for counteracting the transforming effects of various oncogenes.

Tyrosine phosphorylation of p130$^{cas}$ has been observed in fibroblasts following integrin-mediated cell adhesion to extracellular matrix proteins (Nojima et al., *J. Biol. Chem.* 270:15398–15402 (1995); Petch et al., *J. Cell Science* 108:1371–1379 (1995); Vuori and Ruoslahti, *J. Biol. Chem.* 270:22259–22262 (1995)). Under these conditions, using an antibody (4F4) that predominantly recognizes tyrosine phosphorylated p130$^{cas}$ (Kanner et al., *EMBO J.* 10:1689–1698 (1991); Petch et al., *J. Cell Science* 108:1371–1379 (1995)) it was shown that phosphorylated p130$^{cas}$ is localized to focal adhesions (Petch et al., *J. Cell Science* 108:1371–1379 (1995)), whereas fractionation studies have demonstrated that the normal cellular location of the majority of non-phosphorylated p130$^{cas}$ is the cytosol (Sakai et al., *EMBO J.* 13:3748–3756 (1994)). Furthermore, in crk-transformed fibroblasts, tyrosine phosphorylated p130$^{cas}$ is detected only in insoluble fractions (Sakai et al., *EMBO J.* 13:3748–3756

(1994)), suggesting that both cell adhesion- and transformation-mediated phosphorylation of p130$^{cas}$ is associated with redistribution of the protein from the cytosol to focal adhesions.

It is plausible that the redistribution of tyrosine phosphorylated p130$^{cas}$ may be driven by its association with FAK, which is constitutively associated with focal adhesions due to its C-terminal focal adhesion targeting domain (Hildebrand et al., *J. Cell Biol.* 123:993–1005 (1993); Schaller et al., *Proc. Natl. Acad. Sci. USA* 89:5192–5196 (1992)). The sequestration of tyrosine phosphorylated p130$^{cas}$ in focal adhesions both in transformed cells, and following integrin-mediated cell adhesion, strongly suggests a role for p130$^{cas}$ in signalling events in this region of the cell. One consequence of the redistribution of tyrosine phosphorylated p130$^{cas}$ is likely to be that, in addition to localizing p130$^{cas}$ to a region of the cell containing abundant protein tyrosine kinase activity, the phosphorylated protein will be relatively inaccessible to the cytosolic phosphatase PTP-PEST. This raises the possibility that the role of PTP-PEST in dephosphorylating p130$^{cas}$ may be to prevent inappropriate tyrosine phosphorylation of the cytosolic pool of p130$^{cas}$, thus preventing formation of signalling complexes assembled around tyrosine phosphorylated p130$^{cas}$ in inappropriate cellular locations.

Several mitogenic factors potently stimulate tyrosine phosphorylation of p130$^{cas}$. These include agents acting through heterotrimeric G protein-coupled receptors such as lysophosphatidic acid (Seufferlein and Rozengurt, *J. Biol. Chem.* 269:9345–9351 (1994)), bradykinin (Leeb-Lundberg et al., *J. Biol. Chem.* 269: 24328–24344 (1994)), and bombesin (Zachary et al., *J. Biol. Chem.* 267:19031–19034 (1992)), as well as growth factors that activate receptor tyrosine kinases, namely PDGF (Rankin and Rozengurt, *J. Biol. Chem.* 269:704–710 (1994)), EGF and NGF (Ribon and Saltiel, *J. Biol. Chem.* 271:7375–7380 (1996)). These observations suggest roles for p130$^{cas}$ in regulation of mitogenic signalling pathways, presumably involving assembly of signalling complexes based on tyrosine phosphorylated p130$^{cas}$. The identities of the proteins involved in these complexes are not established, but are likely to include SH2 domain-containing adaptor proteins such as crk (Ribon and Saltiel, *J. Biol. Chem.* 271:7375–7380 (1996)), and its associated proteins (Feller et al., *Oncogene* 10:1465–1473 (1995); Hasegawa et al., *Mol. Cell. Biol.* 16:1770–1776 (1996); Knudsen et al., *J. Biol. Chem.* 269:32781–32787 (1994); Matsuda et al., *Mol. Cell. Biol.* 14: 5495–5500 (1994); Tanaka et al., *Proc. Natl. Acad. Sci. USA* 91:3443–3447 (1994)). Therefore tyrosine phosphorylation and dephosphorylation of p130$^{cas}$ potentially plays a central role in regulating the formation of such complexes, thereby influencing downstream events in mitogenic signalling.

Equivalents

Those skilled in the art will recognize, or be able to ascertain, using no more than routine experimentation, many equivalents to the specific embodiments of the invention described herein. Such equivalents are intended to be encompassed by the following claims.

We claim:

1. A method of reducing the activity of a tyrosine phosphorylated protein, comprising administering to a mammal a protein tyrosine phosphatase in which the invariant aspartate residue is replaced with an amino acid which does not cause significant alteration of the Km of the enzyme but which results in a reduction in Kcat to less than 1 per minute, whereby formation of the complex reduces the activity of the tyrosine phosphorylated protein.

2. A method according to claim 1, wherein the tyrosine phosphorylated protein is selected from the group consisting of: p130$^{cas}$, the EGF receptor, p210 bcr:abl, MAP kinase and the insulin receptor.

3. A method according to claim 1, wherein the protein tyrosine phosphatase is selected from the group consisting of: PTP1B, PTP-PEST, PTP$_\gamma$, MKP-1, DEP-1, PTP$\mu$, PTPX1, PTPX10 and PTPH1.

4. A method of reducing the transforming effects of oncogenes associated with p130$^{cas}$ phosphorylation comprising administering to a mammal a protein tyrosine phosphatase which is PTP-PEST or PTP-PEST in which the invariant aspartate residue is replaced with an amino acid which does not cause significant alteration of the Km of the enzyme but which results in a reduction in Kcat to less than 1 per minute, whereby the PTP binds to and/or dephosphorylates p130$^{cas}$, thereby negatively regulating the downstream effects of p130$^{cas}$ and reducing the transforming effects of oncogenes associated with p130$^{cas}$ phosphorylation.

5. A method according to claim 4, wherein the oncogene is selected from the group consisting of: v-crk, v-src and c-Ha-ras.

6. A method of reducing formation of signalling complexes associated with p130$^{cas}$ comprising administering to a mammal a protein tyrosine phosphatase which is PTP-PEST or PTP-PEST in which the invariant aspartate residue is replaced with an amino acid which does not cause significant alteration of the Km of the enzyme but which results in a reduction in Kcat to less than 1 per minute, whereby the PTP binds to and/or dephosphorylates p130$^{cas}$, thereby negatively regulating the downstream effects of p130$^{cas}$ and reducing the formation of signalling complexes associated with p130$^{cas}$.

7. A method according to claim 6, which prevents the induction of mitogenic pathways.

8. A method of reducing cytotoxic effects associated with protein tyrosine phosphatase administration or overexpression, comprising administering to a mammal a protein tyrosine phosphatase in which the invariant aspartate residue is replaced with an amino acid which does not cause significant alteration of the Km of the enzyme but which results in a reduction in Kcat to less than 1 per minute, in place of a corresponding wild type protein tyrosine phosphatase.

* * * * *

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 196 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Asp Phe Pro Cys Arg Val Ala Lys Leu Pro Lys Asn Lys Asn Arg Asn
 1               5                  10                  15

Arg Tyr Arg Asp Val Ser Pro Phe Asp His Ser Arg Ile Lys Leu His
            20                  25                  30

Gln Glu Asp Asn Asp Tyr Ile Asn Ala Ser Leu Ile Lys Met Glu Glu
        35                  40                  45

Ala Gln Arg Ser Tyr Ile Leu Thr Gln Gly Pro Leu Pro Asn Thr Cys
    50                  55                  60

Gly His Phe Trp Glu Met Val Trp Glu Gln Lys Ser Arg Gly Val Val
65                  70                  75                  80

Met Leu Asn Arg Val Met Glu Lys Gly Ser Leu Lys Cys Ala Gln Tyr
                85                  90                  95

Trp Pro Gln Lys Glu Glu Lys Glu Met Ile Phe Glu Asp Thr Asn Leu
                100                 105                 110

Lys Leu Thr Leu Ile Ser Glu Asp Ile Lys Ser Tyr Tyr Thr Val Leu
            115                 120                 125
```

```
Glu Leu Glu Asn Leu Thr Thr Gln Gly Thr Arg Glu Ile Leu His Phe
        130                 135                 140
His Tyr Thr Thr Trp Pro Asp Phe Gly Val Pro Glu Ser Pro Ala Ser
145                 150                 155                 160
Phe Leu Asn Phe Leu Phe Lys Val Arg Glu Ser Gly Ser Leu Ser Pro
                165                 170                 175
Glu His Gly Pro Val Val Val His Cys Ser Ala Gly Ile Gly Arg Ser
                180                 185                 190
Gly Thr Phe Cys
        195
```

(2) INFORMATION FOR SEQ ID NO:2:

(i) SEQUENCE CHARACTERISTICS:
        (A) LENGTH: 194 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Asp Tyr Pro His Arg Val Ala Lys Phe Pro Glu Asn Arg Asn Arg Asn
1                   5                   10                  15
Arg Tyr Arg Asp Val Ser Pro Tyr Asp His Ser Arg Val Leu Gln Asn
                20                  25                  30
Ala Glu Asn Asp Tyr Ile Asn Ala Ser Leu Val Asp Ile Glu Glu Ala
            35                  40                  45
Gln Arg Ser Tyr Ile Leu Thr Gln Gly Pro Leu Pro Asn Thr Cys Cys
        50                  55                  60
His Phe Trp Leu Met Val Trp Gln Gln Lys Thr Lys Ala Val Val Met
65                  70                  75                  80
Leu Asn Arg Ile Val Glu Lys Glu Ser Val Lys Cys Ala Gln Tyr Trp
                85                  90                  95
Pro Thr Asp Asp Gln Glu Met Leu Phe Lys Glu Thr Gly Phe Ser Val
                100                 105                 110
Lys Leu Leu Ser Glu Asp Val Lys Ser Tyr Tyr Thr Val Leu Gln Leu
            115                 120                 125
Glu Asn Ile Asn Ser Gly Glu Thr Arg Thr Ile Ser His Phe His Tyr
        130                 135                 140
Thr Thr Trp Pro Asp Phe Gly Val Pro Glu Ser Pro Ala Ser Phe Leu
145                 150                 155                 160
Asn Phe Leu Phe Lys Val Arg Glu Ser Gly Ser Leu Asn Pro Asp His
                165                 170                 175
Gly Pro Ala Val Ile His Cys Ser Ala Gly Ile Gly Arg Ser Gly Thr
                180                 185                 190
Phe Ser
```

(2) INFORMATION FOR SEQ ID NO:3:

(i) SEQUENCE CHARACTERISTICS:
        (A) LENGTH: 261 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Gly Ile Thr Ala Asp Ser Ser Asn His Pro Asp Asn Lys His Lys Asn
1               5                   10                  15

Arg Tyr Ile Asn Ile Val Ala Tyr Asp His Ser Arg Val Lys Leu Ala
                20                  25                  30

Gln Leu Ala Glu Lys Asp Gly Lys Leu Thr Asp Tyr Ile Asn Ala Asn
            35                  40                  45

Tyr Val Asp Gly Tyr Asn Arg Pro Lys Ala Tyr Ile Ala Ala Gln Gly
50                      55                  60

Pro Leu Lys Ser Thr Ala Glu Asp Phe Trp Arg Met Ile Trp Glu His
65                  70                  75                  80

Asn Val Glu Val Ile Val Met Ile Thr Asn Leu Val Glu Lys Gly Arg
                85                  90                  95

Arg Lys Cys Asp Gln Tyr Trp Pro Pro Ala Asp Gly Ser Glu Glu Tyr
            100                 105                 110

Gly Asn Phe Leu Val Thr Gln Lys Ser Val Gln Val Leu Ala Tyr Tyr
            115                 120                 125

Thr Val Phe Thr Leu Arg Asn Thr Lys Ile Lys Lys Gly Ser Gln Lys
            130                 135                 140

Gly Arg Pro Ser Gly Arg Val Val Thr Gln Tyr His Tyr Thr Gln Trp
145                 150                 155                 160

Pro Asp Met Gly Val Pro Glu Tyr Ser Leu Pro Val Leu Thr Phe Val
                165                 170                 175

Arg Lys Ala Ala Tyr Ala Lys Arg His Ala Val Gly Pro Val Val Val
            180                 185                 190

His Cys Ser Ala Gly Val Gly Arg Thr Gly Thr Tyr Ile Val Leu Asp
            195                 200                 205

Ser Met Leu Gln Gln Ile Gln His Glu Gly Thr Val Asn Ile Phe Gly
            210                 215                 220

Phe Leu Lys His Ile Arg Ser Gln Arg Asn Tyr Leu Val Gln Thr Glu
225                 230                 235                 240

Glu Gln Tyr Val Phe Ile His Asp Thr Leu Val Glu Ala Ile Leu Ser
                245                 250                 255

Lys Glu Thr Glu Val
            260

(2) INFORMATION FOR SEQ ID NO:4:

(i) SEQUENCE CHARACTERISTICS:
        (A) LENGTH: 260 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Gly Ile Thr Ala Asp Ser Ser Asn His Pro Asp Asn Lys His Lys Asn
1               5                   10                  15

Arg Tyr Ile Asn Ile Val Ala Tyr Asp His Ser Arg Val Lys Leu Ala
                20                  25                  30

Gln Leu Ala Glu Lys Asp Gly Lys Leu Thr Asp Tyr Ile Asn Ala Asn
            35                  40                  45

Tyr Val Asp Gly Tyr Asn Arg Pro Lys Ala Tyr Ile Ala Ala Gln Gly
50                      55                  60

Pro Leu Lys Ser Thr Ala Glu Asp Phe Trp Arg Met Ile Trp Glu His
65                  70                  75                  80

Asn Val Glu Val Ile Val Met Ile Thr Asn Leu Val Glu Lys Gly Arg

```
                        85                  90                  95
Arg Lys Cys Asp Gln Tyr Trp Pro Ala Asp Gly Ser Glu Glu Tyr Gly
                100                 105                 110

Asn Phe Leu Val Thr Gln Lys Ser Val Gln Val Leu Ala Tyr Tyr Thr
            115                 120                 125

Val Phe Thr Leu Arg Asn Thr Lys Ile Lys Lys Gly Ser Gln Lys Gly
        130                 135                 140

Arg Pro Ser Gly Arg Val Val Thr Gln Tyr His Tyr Thr Gln Trp Pro
145                 150                 155                 160

Asp Met Gly Val Pro Glu Tyr Ser Leu Pro Val Leu Thr Phe Val Arg
                165                 170                 175

Lys Ala Ala Tyr Ala Lys Arg His Ala Val Gly Pro Val Val His
            180                 185                 190

Cys Ser Ala Gly Val Gly Arg Thr Gly Thr Tyr Ile Val Leu Asp Ser
        195                 200                 205

Met Leu Gln Gln Ile Gln His Glu Gly Thr Val Asn Ile Phe Gly Phe
    210                 215                 220

Leu Lys His Ile Arg Ser Gln Arg Asn Tyr Leu Val Gln Thr Glu Glu
225                 230                 235                 240

Gln Tyr Val Phe Ile His Asp Thr Leu Val Glu Ala Ile Leu Ser Lys
                245                 250                 255

Glu Thr Glu Val
            260

(2) INFORMATION FOR SEQ ID NO:5:

(i) SEQUENCE CHARACTERISTICS:
        (A) LENGTH: 263 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Asn Ile Thr Ala Glu His Ser Asn His Pro Glu Asn Lys His Lys Asn
1               5                   10                  15

Arg Tyr Ile Asn Ile Leu Ala Tyr Asp His Ser Arg Val Lys Leu Arg
            20                  25                  30

Pro Leu Pro Gly Lys Asp Ser Lys His Ser Asp Tyr Ile Asn Ala Asn
        35                  40                  45

Tyr Val Asp Gly Tyr Asn Lys Ala Lys Ala Tyr Ile Ala Thr Gln Gly
    50                  55                  60

Pro Leu Lys Ser Thr Phe Glu Asp Phe Trp Arg Met Ile Trp Glu Gln
65                  70                  75                  80

Asn Thr Gly Ile Ile Val Met Ile Thr Asn Leu Val Glu Lys Gly Arg
                85                  90                  95

Arg Lys Cys Asp Gln Tyr Trp Pro Thr Glu Asn Ser Glu Glu Tyr Gly
                100                 105                 110

Asn Ile Ile Val Thr Leu Lys Ser Thr Lys Ile His Ala Cys Tyr Thr
            115                 120                 125

Val Phe Ser Ile Arg Asn Thr Lys Val Lys Lys Gly Gln Lys Gly Asn
        130                 135                 140

Pro Lys Gly Arg Gln Asn Glu Arg Val Val Ile Gln Tyr His Tyr Thr
145                 150                 155                 160

Gln Trp Pro Asp Met Gly Val Pro Glu Tyr Ala Leu Pro Val Leu Thr
                165                 170                 175
```

```
Phe Val Arg Arg Ser Ser Ala Ala Arg Met Pro Glu Thr Gly Pro Val
            180                 185                 190

Leu Val His Cys Ser Ala Gly Val Gly Arg Thr Gly Thr Tyr Ile Val
            195                 200                 205

Ile Asp Ser Met Leu Gln Gln Ile Lys Asp Lys Ser Thr Val Asn Val
            210                 215                 220

Leu Gly Phe Leu Lys His Ile Arg Thr Gln Arg Asn Tyr Leu Val Gln
225                 230                 235                 240

Thr Glu Glu Gln Tyr Ile Phe Ile His Asp Ala Leu Leu Glu Ala Ile
            245                 250                 255

Leu Gly Lys Glu Thr Glu Val
            260
```

(2) INFORMATION FOR SEQ ID NO:6:

(i) SEQUENCE CHARACTERISTICS:
        (A) LENGTH: 257 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Asp Leu Pro Cys Glu His Ser Gln His Pro Glu Asn Lys Arg Lys Asn
1                   5                   10                  15

Arg Tyr Leu Asn Ile Thr Ala Tyr Asp His Ser Arg Val His Leu His
            20                  25                  30

Pro Thr Pro Gly Gln Lys Lys Asn Leu Asp Tyr Ile Asn Ala Asn Phe
            35                  40                  45

Ile Asp Gly Tyr Gln Lys Gly His Ala Phe Ile Gly Thr Gln Gly Pro
50                  55                  60

Leu Pro Asp Thr Phe Asp Cys Phe Trp Arg Met Ile Trp Glu Gln Arg
65                  70                  75                  80

Val Ala Ile Ile Val Met Ile Thr Asn Leu Val Glu Arg Gly Arg Arg
            85                  90                  95

Lys Cys Asp Met Tyr Trp Pro Lys Asp Gly Val Glu Thr Tyr Gly Val
            100                 105                 110

Ile Gln Val Lys Leu Ile Glu Glu Val Met Ser Thr Tyr Thr Val
            115                 120                 125

Leu Gln Ile Lys His Leu Lys Leu Lys Lys Lys Gln Cys Asn Thr
130                 135                 140

Glu Lys Leu Val Tyr Gln Tyr His Tyr Thr Asn Trp Pro Asp His Gly
145                 150                 155                 160

Thr Pro Asp His Pro Leu Pro Val Leu Asn Phe Val Lys Lys Ser Ser
            165                 170                 175

Ala Ala Asn Pro Ala Glu Ala Gly Pro Ile Val Val His Cys Ser Ala
            180                 185                 190

Gly Val Gly Arg Thr Gly Thr Tyr Ile Val Leu Asp Ala Met Leu Lys
            195                 200                 205

Gln Ile Gln Gln Lys Asn Ile Val Asn Val Phe Gly Phe Leu Arg His
            210                 215                 220

Ile Arg Ala Gln Arg Asn Phe Leu Val Gln Thr Glu Glu Gln Tyr Ile
225                 230                 235                 240

Phe Leu His Asp Ala Leu Val Glu Ala Ile Ala Ser Gly Glu Thr Asn
            245                 250                 255
```

Leu (2) INFORMATION FOR SEQ ID NO:7:

(i) SEQUENCE CHARACTERISTICS:
        (A) LENGTH: 250 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Gln Phe Thr Trp Glu Asn Ser Asn Leu Glu Val Asn Lys Pro Lys Asn
 1               5                  10                  15

Arg Tyr Ala Asn Val Ile Ala Tyr Asp His Ser Arg Val Ile Leu Thr
            20                  25                  30

Ser Ile Asp Gly Val Pro Gly Ser Asp Tyr Ile Asn Ala Asn Tyr Ile
        35                  40                  45

Asp Gly Tyr Arg Lys Gln Asn Ala Tyr Ile Ala Thr Gln Gly Pro Leu
50                  55                  60

Pro Glu Thr Met Gly Asp Phe Trp Arg Met Val Trp Glu Gln Arg Thr
65                  70                  75                  80

Ala Thr Val Val Met Met Thr Arg Leu Glu Glu Lys Ser Arg Val Lys
                85                  90                  95

Cys Asp Gln Tyr Trp Pro Ala Arg Gly Thr Glu Thr Cys Gly Leu Ile
                100                 105                 110

Gln Val Thr Leu Leu Asp Thr Val Glu Leu Ala Thr Tyr Thr Val Phe
            115                 120                 125

Ala Leu His Lys Ser Gly Ser Ser Glu Lys Arg Glu Leu Arg Gln Phe
        130                 135                 140

Gln Phe Met Ala Trp Pro Asp His Gly Val Pro Glu Tyr Pro Thr Pro
145                 150                 155                 160

Ile Leu Ala Phe Leu Arg Arg Val Lys Ala Cys Asn Pro Leu Asp Ala
                165                 170                 175

Gly Pro Met Val Val His Cys Ser Ala Gly Val Gly Arg Thr Gly Cys
                180                 185                 190

Phe Ile Val Ile Asp Ala Met Leu Glu Arg Met Lys His Glu Lys Thr
            195                 200                 205

Val Asp Ile Tyr Gly His Val Thr Cys Met Arg Ser Gln Arg Asn Tyr
        210                 215                 220

Met Val Gln Thr Glu Asp Gln Tyr Val Phe Ile His Glu Ala Leu Leu
225                 230                 235                 240

Glu Ala Ala Thr Cys Gly His Thr Glu Val
                245                 250
```

(2) INFORMATION FOR SEQ ID NO:8:

(i) SEQUENCE CHARACTERISTICS:
        (A) LENGTH: 249 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Ser Ala Pro Trp Asp Ser Ala Lys Lys Asp Glu Asn Arg Met Lys Asn
 1               5                  10                  15

Arg Tyr Gly Asn Ile Ile Ala Tyr Asp His Ser Arg Val Arg Leu Gln
```

```
                     20                  25                  30
Thr Ile Glu Gly Asp Thr Asn Ser Asp Tyr Ile Asn Gly Asn Tyr Ile
                 35                  40                  45
Asp Gly Tyr His Arg Pro Asn His Tyr Ile Ala Thr Gln Gly Pro Met
 50                  55                  60
Gln Glu Thr Ile Tyr Asp Phe Trp Arg Met Val Trp His Glu Asn Thr
 65                  70                  75                  80
Ala Ser Ile Ile Met Val Thr Asn Leu Val Glu Val Gly Arg Val Lys
                 85                  90                  95
Cys Cys Lys Tyr Trp Pro Asp Asp Thr Glu Ile Tyr Lys Asp Ile Lys
                100                 105                 110
Val Thr Leu Ile Glu Thr Glu Leu Leu Ala Glu Tyr Val Ile Phe Ala
                115                 120                 125
Val Glu Lys Arg Gly Val His Glu Ile Arg Glu Ile Arg Gln Phe His
 130                 135                 140
Phe Thr Gly Trp Pro Asp His Gly Val Pro Tyr His Ala Thr Gly Leu
 145                 150                 155                 160
Leu Gly Phe Val Arg Gln Val Lys Ser Lys Ser Pro Pro Ser Ala Gly
                165                 170                 175
Pro Leu Val Val His Cys Ser Ala Gly Ala Gly Arg Thr Gly Cys Phe
                180                 185                 190
Ile Val Ile Asp Ile Met Leu Asp Met Ala Glu Arg Glu Gly Val Val
                195                 200                 205
Asp Ile Tyr Asn Cys Val Arg Glu Leu Arg Ser Arg Arg Val Asn Met
                210                 215                 220
Val Gln Thr Glu Glu Gln Tyr Val Phe Ile His Asp Ala Ile Leu Glu
 225                 230                 235                 240
Ala Cys Leu Cys Gly Asp Thr Ser Val
                245

(2) INFORMATION FOR SEQ ID NO:9:

(i) SEQUENCE CHARACTERISTICS:
        (A) LENGTH: 254 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Gln Ala Thr Cys Glu Ala Ala Ser Lys Glu Glu Asn Lys Glu Lys Asn
  1               5                  10                  15
Arg Tyr Val Asn Ile Leu Pro Tyr Asp His Ser Arg Val His Leu Thr
                 20                  25                  30
Pro Val Glu Gly Val Pro Asp Ser Asp Tyr Ile Asn Ala Ser Phe Ile
                 35                  40                  45
Asn Gly Tyr Gln Glu Lys Asn Lys Phe Ile Ala Ala Gln Gly Pro Lys
 50                  55                  60
Glu Glu Thr Val Asn Asp Phe Trp Arg Met Ile Trp Gln Glu Asn Thr
 65                  70                  75                  80
Ala Thr Ile Val Met Val Thr Asn Leu Lys Glu Arg Lys Glu Cys Lys
                 85                  90                  95
Cys Ala Gln Tyr Trp Pro Asp Gln Gly Cys Trp Thr Tyr Gly Asn Ile
                100                 105                 110
Arg Val Ser Val Glu Asp Val Thr Val Leu Val Asp Tyr Thr Val Phe
                115                 120                 125
```

```
Cys Ile Gln Gln Val Gly Asp Met Thr Asn Arg Lys Pro Gln Arg Leu
    130                 135                 140

Ile Thr Gln Phe His Phe Thr Ser Trp Pro Asp Phe Gly Val Pro Phe
145                 150                 155                 160

Thr Pro Ile Gly Met Leu Lys Phe Leu Lys Lys Val Lys Ala Cys Asn
                165                 170                 175

Pro Gln Tyr Ala Gly Ala Ile Val Val His Cys Ser Ala Gly Val Gly
            180                 185                 190

Arg Thr Gly Thr Phe Val Val Ile Asp Ala Met Leu Asp Met Met His
            195                 200                 205

Thr Glu Arg Lys Val Asp Val Tyr Gly Phe Val Ser Arg Ile Arg Ala
    210                 215                 220

Gln Arg Cys Gln Met Val Gln Thr Asp Met Gln Tyr Val Phe Ile Tyr
225                 230                 235                 240

Gln Ala Leu Leu Glu His Tyr Leu Tyr Gly Asp Thr Glu Leu
                245                 250
```

(2) INFORMATION FOR SEQ ID NO:10:

(i) SEQUENCE CHARACTERISTICS:
        (A) LENGTH: 253 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Gln Gly Thr Phe Glu Leu Ala Asn Lys Glu Asn Arg Glu Lys Asn
1               5                   10                  15

Arg Tyr Pro Asn Ile Leu Pro Asn Asp His Ser Arg Val Ile Leu Ser
                20                  25                  30

Gln Leu Asp Gly Ile Pro Cys Ser Asp Tyr Ile Asn Ala Ser Tyr Ile
            35                  40                  45

Asp Gly Tyr Lys Glu Lys Asn Lys Phe Ile Ala Ala Gln Gly Pro Lys
        50                  55                  60

Gln Glu Thr Val Asn Asp Phe Trp Arg Met Val Trp Glu Gln Lys Ser
65                  70                  75                  80

Ala Thr Ile Val Met Leu Thr Asn Leu Lys Glu Arg Lys Glu Glu Lys
                85                  90                  95

Cys His Gln Tyr Trp Pro Asp Gly Cys Trp Thr Tyr Gly Asn Ile
            100                 105                 110

Arg Val Cys Val Glu Asp Cys Val Val Leu Val Asp Tyr Thr Ile Phe
        115                 120                 125

Cys Ile Gln Pro Gln Leu Pro Asp Gly Cys Lys Ala Pro Arg Leu Val
    130                 135                 140

Ser Gln Leu His Phe Thr Ser Trp Pro Asp Phe Gly Val Pro Phe Thr
145                 150                 155                 160

Pro Ile Gly Met Leu Lys Phe Leu Lys Lys Val Lys Thr Leu Asn Pro
                165                 170                 175

Val His Ala Gly Pro Ile Val Val His Cys Ser Ala Gly Val Gly Arg
            180                 185                 190

Thr Gly Thr Phe Ile Val Ile Asp Ala Met Met Ala Met Met His Ala
            195                 200                 205

Glu Gln Lys Val Asp Val Phe Glu Phe Val Ser Arg Ile Arg Asn Gln
    210                 215                 220
```

```
Arg Pro Gln Met Val Gln Thr Asp Met Gln Tyr Thr Phe Ile Tyr Gln
225                 230                 235                 240

Ala Leu Leu Glu Tyr Tyr Leu Tyr Gly Asp Thr Glu Leu
                245                 250
```

(2) INFORMATION FOR SEQ ID NO:11:

(i) SEQUENCE CHARACTERISTICS:
        (A) LENGTH: 253 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Lys Phe Pro Ile Lys Asp Ala Arg Lys Pro His Asn Gln Asn Lys Asn
1               5                   10                  15

Arg Tyr Val Asp Ile Leu Pro Tyr Asp Tyr Asn Arg Val Glu Leu Ser
                20                  25                  30

Glu Ile Asn Gly Asp Ala Gly Ser Thr Tyr Ile Asn Ala Ser Tyr Ile
                35                  40                  45

Asp Gly Phe Lys Glu Pro Arg Lys Tyr Ile Ala Ala Gln Gly Pro Arg
            50                  55                  60

Asp Glu Thr Val Asp Asp Phe Trp Arg Met Ile Trp Glu Gln Lys Ala
65                  70                  75                  80

Thr Val Ile Val Met Val Thr Arg Cys Glu Glu Gly Asn Arg Asn Lys
                    85                  90                  95

Cys Ala Glu Tyr Trp Pro Ser Met Glu Glu Gly Thr Arg Ala Phe Lys
                100                 105                 110

Asp Ile Val Val Thr Ile Asn Asp His Lys Arg Cys Pro Asp Tyr Ile
            115                 120                 125

Ile Leu Asn Val Ala His Lys Lys Glu Lys Ala Thr Gly Arg Glu Val
            130                 135                 140

Thr His Ile Gln Phe Thr Ser Trp Pro Asp His Gly Val Pro Glu Asp
145                 150                 155                 160

Pro His Leu Leu Leu Lys Leu Arg Arg Arg Val Asn Ala Phe Ser Asn
                165                 170                 175

Phe Phe Ser Gly Pro Ile Val Val His Cys Ser Ala Gly Val Gly Arg
                180                 185                 190

Thr Gly Thr Tyr Ile Gly Ile Asp Ala Met Leu Glu Gly Leu Glu Ala
            195                 200                 205

Glu Gly Lys Val Asp Val Tyr Gly Tyr Val Val Lys Leu Arg Arg Gln
        210                 215                 220

Arg Cys Leu Met Val Gln Val Glu Ala Gln Tyr Ile Leu Ile His Gln
225                 230                 235                 240

Ala Leu Val Glu Tyr Asn Gln Phe Gly Glu Thr Glu Val
                245                 250
```

(2) INFORMATION FOR SEQ ID NO:12:

(i) SEQUENCE CHARACTERISTICS:
        (A) LENGTH: 266 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

| Leu | Tyr | Ser | Arg | Lys | Glu | Gly | Gln | Arg | Gln | Glu | Asn | Lys | Asn | Lys | Asn |
|---|---|---|---|---|---|---|---|---|---|---|---|---|---|---|---|
| 1 | | | | 5 | | | | | 10 | | | | | 15 | |

| Arg | Tyr | Lys | Asn | Ile | Leu | Pro | Phe | Asp | His | Thr | Arg | Val | Val | Leu | His |
|---|---|---|---|---|---|---|---|---|---|---|---|---|---|---|---|
| | | | 20 | | | | | 25 | | | | | 30 | | |

| Asp | Gly | Asp | Pro | Asn | Glu | Pro | Val | Ser | Asp | Tyr | Ile | Asn | Ala | Asn | Ile |
|---|---|---|---|---|---|---|---|---|---|---|---|---|---|---|---|
| | | 35 | | | | | 40 | | | | | 45 | | | |

| Ile | Met | Pro | Glu | Phe | Glu | Thr | Lys | Cys | Asn | Asn | Ser | Lys | Pro | Lys | Lys |
|---|---|---|---|---|---|---|---|---|---|---|---|---|---|---|---|
| 50 | | | | | 55 | | | | | 60 | | | | | |

| Ser | Tyr | Ile | Ala | Thr | Gln | Gly | Cys | Leu | Gln | Asn | Thr | Val | Asn | Asp | Phe |
|---|---|---|---|---|---|---|---|---|---|---|---|---|---|---|---|
| 65 | | | | | 70 | | | | | 75 | | | | | 80 |

| Trp | Arg | Met | Val | Phe | Gln | Glu | Asn | Ser | Arg | Val | Ile | Val | Met | Thr | Thr |
|---|---|---|---|---|---|---|---|---|---|---|---|---|---|---|---|
| | | | | 85 | | | | | 90 | | | | | 95 | |

| Lys | Glu | Val | Glu | Arg | Gly | Lys | Ser | Lys | Cys | Val | Lys | Tyr | Trp | Pro | Asp |
|---|---|---|---|---|---|---|---|---|---|---|---|---|---|---|---|
| | | | 100 | | | | | 105 | | | | | 110 | | |

| Glu | Tyr | Ala | Leu | Lys | Glu | Tyr | Gly | Val | Met | Arg | Val | Arg | Asn | Val | Lys |
|---|---|---|---|---|---|---|---|---|---|---|---|---|---|---|---|
| | | | 115 | | | | | 120 | | | | | 125 | | |

| Glu | Ser | Ala | Ala | His | Asp | Tyr | Thr | Leu | Leu | Lys | Leu | Ser | Lys | Val | Gly |
|---|---|---|---|---|---|---|---|---|---|---|---|---|---|---|---|
| | | 130 | | | | | 135 | | | | | 140 | | | |

| Gln | Gly | Asn | Thr | Glu | Arg | Thr | Val | Trp | Gln | Tyr | His | Phe | Arg | Thr | Trp |
|---|---|---|---|---|---|---|---|---|---|---|---|---|---|---|---|
| 145 | | | | | 150 | | | | | 155 | | | | | 160 |

| Pro | Asp | His | Gly | Val | Pro | Ser | Asp | Pro | Gly | Gly | Val | Leu | Asp | Phe | Leu |
|---|---|---|---|---|---|---|---|---|---|---|---|---|---|---|---|
| | | | | 165 | | | | | 170 | | | | | 175 | |

| Glu | Glu | Val | His | His | Lys | Gln | Glu | Ser | Ile | Met | Asp | Ala | Gly | Pro | Val |
|---|---|---|---|---|---|---|---|---|---|---|---|---|---|---|---|
| | | | 180 | | | | | 185 | | | | | 190 | | |

| Val | Val | His | Cys | Ser | Ala | Gly | Ile | Gly | Arg | Thr | Gly | Thr | Phe | Ile | Val |
|---|---|---|---|---|---|---|---|---|---|---|---|---|---|---|---|
| | | 195 | | | | | 200 | | | | | 205 | | | |

| Ile | Asp | Ile | Leu | Ile | Asp | Ile | Arg | Glu | Lys | Gly | Val | Asp | Cys | Asp |
|---|---|---|---|---|---|---|---|---|---|---|---|---|---|---|
| | 210 | | | | | 215 | | | | | 220 | | | |

| Ile | Asp | Val | Pro | Lys | Thr | Ile | Gln | Met | Val | Arg | Ser | Gln | Arg | Ser | Gly |
|---|---|---|---|---|---|---|---|---|---|---|---|---|---|---|---|
| 225 | | | | | 230 | | | | | 235 | | | | | 240 |

| Met | Val | Gln | Thr | Glu | Ala | Gln | Tyr | Arg | Phe | Ile | Tyr | Met | Ala | Val | Gln |
|---|---|---|---|---|---|---|---|---|---|---|---|---|---|---|---|
| | | | | 245 | | | | | 250 | | | | | 255 | |

| His | Tyr | Ile | Glu | Thr | Leu | Gln | Arg | Arg | Ile |
|---|---|---|---|---|---|---|---|---|---|
| | | | | 260 | | | | | 265 |

(2) INFORMATION FOR SEQ ID NO:13:

(i) SEQUENCE CHARACTERISTICS:
        (A) LENGTH: 263 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

| Leu | His | Gln | Arg | Leu | Glu | Gly | Gln | Arg | Pro | Glu | Asn | Lys | Gly | Lys | Asn |
|---|---|---|---|---|---|---|---|---|---|---|---|---|---|---|---|
| 1 | | | | 5 | | | | | 10 | | | | | 15 | |

| Arg | Tyr | Lys | Asn | Ile | Leu | Pro | Phe | Asp | His | Ser | Arg | Val | Ile | Leu | Gln |
|---|---|---|---|---|---|---|---|---|---|---|---|---|---|---|---|
| | | | 20 | | | | | 25 | | | | | 30 | | |

| Gly | Arg | Asp | Ser | Asn | Ile | Pro | Gly | Ser | Asp | Tyr | Ile | Asn | Ala | Asn | Tyr |
|---|---|---|---|---|---|---|---|---|---|---|---|---|---|---|---|
| | | 35 | | | | | 40 | | | | | 45 | | | |

| Ile | Lys | Asn | Gln | Leu | Leu | Gly | Pro | Asp | Glu | Asn | Ala | Lys | Thr | Tyr | Ile |
|---|---|---|---|---|---|---|---|---|---|---|---|---|---|---|---|
| 50 | | | | | 55 | | | | | 60 | | | | | |

| Ala | Ser | Gln | Gly | Cys | Leu | Glu | Ala | Thr | Val | Asn | Asp | Phe | Trp | Gln | Met |
|---|---|---|---|---|---|---|---|---|---|---|---|---|---|---|---|
| 65 | | | | | 70 | | | | | 75 | | | | | 80 |

| Ala | Trp | Gln | Glu | Asn | Ser | Arg | Val | Ile | Val | Met | Thr | Thr | Arg | Glu | Val |

```
                         85                  90                  95
Glu Lys Gly Arg Asn Lys Cys Val Pro Tyr Trp Pro Glu Val Gly Met
                    100                 105                 110

Gln Arg Ala Tyr Gly Pro Tyr Ser Val Thr Asn Cys Gly Glu His Asp
                115                 120                 125

Thr Thr Glu Tyr Lys Leu Leu Gln Val Ser Pro Leu Asp Asn Gly Asp
            130                 135                 140

Leu Ile Arg Glu Ile Trp His Tyr Gln Tyr Leu Ser Trp Pro Asp His
145                 150                 155                 160

Gly Val Pro Ser Glu Pro Gly Gly Val Leu Ser Phe Leu Asp Gln Ile
                165                 170                 175

Asn Gln Arg Gln Glu Ser Leu Pro His Ala Gly Pro Ile Ile Val His
                180                 185                 190

Cys Ser Ala Gly Ile Gly Arg Thr Gly Thr Ile Ile Val Ile Asp Met
                195                 200                 205

Leu Met Glu Asn Ile Ser Thr Lys Gly Leu Asp Cys Asp Ile Asp Ile
210                 215                 220

Gln Lys Thr Ile Gln Met Val Arg Ala Gln Arg Ser Gly Met Val Gln
225                 230                 235                 240

Thr Glu Ala Gln Tyr Lys Phe Ile Tyr Val Ala Ile Ala Gln Phe Ile
                245                 250                 255

Glu Thr Thr Lys Lys Lys Leu
                260

(2) INFORMATION FOR SEQ ID NO:14:

(i) SEQUENCE CHARACTERISTICS:
        (A) LENGTH: 254 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Asn Gln Ser Cys Asp Ile Ala Leu Leu Pro Glu Asn Arg Gly Lys Asn
1               5                   10                  15

Arg Tyr Asn Asn Ile Leu Pro Tyr Asp Ala Thr Arg Val Lys Leu Ser
                20                  25                  30

Asn Val Asp Asp Asp Pro Cys Ser Asp Tyr Ile Asn Ala Ser Tyr Ile
            35                  40                  45

Pro Gly Asn Asn Phe Arg Arg Glu Tyr Ile Val Thr Gln Gly Pro Leu
50                  55                  60

Pro Gly Thr Lys Asp Asp Phe Trp Lys Met Val Trp Glu Gln Asn Val
65                  70                  75                  80

His Asn Ile Val Met Val Thr Gln Cys Val Glu Lys Gly Arg Val Lys
                85                  90                  95

Cys Asp His Tyr Trp Pro Ala Asp Gln Asp Ser Leu Tyr Tyr Gly Asp
                100                 105                 110

Leu Ile Leu Gln Met Leu Ser Glu Ser Val Leu Pro Glu Trp Thr Ile
            115                 120                 125

Phe Lys Ile Cys Gly Glu Glu Gln Leu Asp Ala His Arg Leu Ile Arg
            130                 135                 140

His Phe His Tyr Thr Val Trp Pro Asp His Gly Val Pro Glu Thr Thr
145                 150                 155                 160

Gln Ser Leu Ile Gln Phe Val Arg Thr Val Arg Asp Tyr Ile Asn Arg
                165                 170                 175
```

```
Ser Pro Gly Ala Gly Pro Thr Val Val His Cys Ser Ala Gly Val Gly
            180                 185                 190

Arg Thr Gly Thr Phe Ile Ala Leu Asp Arg Ile Leu Gln Gln Leu Asp
            195                 200                 205

Ser Lys Asp Ser Val Asp Ile Tyr Gly Ala Val His Asp Leu Arg Leu
            210                 215                 220

His Arg Val His Met Val Gln Thr Glu Cys Gln Tyr Val Tyr Leu His
225                 230                 235                 240

Gln Cys Val Arg Asp Val Leu Arg Ala Arg Lys Leu Arg Ser
                245                 250
```

(2) INFORMATION FOR SEQ ID NO:15:

(i) SEQUENCE CHARACTERISTICS:
        (A) LENGTH: 251 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Asp Gln Pro Cys Thr Phe Ala Asp Leu Pro Cys Asn Arg Pro Lys Asn
1               5                   10                  15

Arg Phe Thr Asn Ile Leu Pro Tyr Asp His Ser Arg Phe Lys Leu Gln
            20                  25                  30

Pro Val Asp Asp Asp Glu Gly Ser Asp Tyr Ile Asn Ala Asn Tyr Val
            35                  40                  45

Pro Gly His Asn Ser Pro Arg Glu Phe Ile Val Thr Gln Gly Pro Leu
            50                  55                  60

His Ser Thr Arg Asp Asp Phe Trp Arg Met Cys Trp Glu Ser Asn Ser
65                  70                  75                  80

Arg Ala Ile Val Met Leu Thr Arg Cys Phe Glu Lys Gly Arg Glu Lys
            85                  90                  95

Cys Asp Gln Tyr Trp Pro Asn Asp Thr Val Pro Val Phe Tyr Gly Asp
                100                 105                 110

Ile Lys Val Gln Ile Leu Asn Asp Ser His Tyr Ala Asp Trp Val Met
            115                 120                 125

Phe Met Leu Cys Arg Gly Ser Glu Gln Arg Ile Leu Arg His Phe His
130                 135                 140

Phe Thr Thr Trp Pro Asp Phe Gly Val Pro Asn Pro Pro Gln Thr Leu
145                 150                 155                 160

Val Arg Phe Val Arg Ala Phe Arg Asp Arg Ile Cys Ala Glu Gln Arg
            165                 170                 175

Pro Ile Val Val His Cys Ser Ala Gly Val Gly Arg Ser Gly Thr Phe
            180                 185                 190

Ile Thr Leu Asp Arg Ile Leu Gln Gln Ile Asn Thr Ser Asp Tyr Val
            195                 200                 205

Asp Ile Phe Gly Ile Val Tyr Ala Met Arg Lys Glu Arg Val Trp Met
            210                 215                 220

Val Gln Thr Glu Gln Gln Tyr Ile Cys Ile His Gln Cys Leu Leu Ala
225                 230                 235                 240

Val Leu Glu Gly Lys Glu Asn Ile Val Gly Pro
                245                 250
```

(2) INFORMATION FOR SEQ ID NO:16:

(i) SEQUENCE CHARACTERISTICS:
    (A) LENGTH: 255 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:16:

```
Ser Gln Ser Gln Met Val Ala Ser Ala Ser Glu Asn Asn Ala Lys Asn
1               5                   10                  15

Arg Tyr Arg Asn Val Leu Pro Tyr Asp Trp Ser Arg Val Pro Leu Lys
            20                  25                  30

Pro Ile His Glu Glu Pro Gly Ser Asp Tyr Ile Asn Ala Ser Phe Met
        35                  40                  45

Pro Gly Leu Trp Ser Pro Gln Glu Phe Ile Ala Thr Gln Gly Pro Leu
    50                  55                  60

Pro Gln Thr Val Gly Asp Phe Trp Arg Leu Val Trp Glu Gln Gln Ser
65                  70                  75                  80

His Thr Leu Val Met Leu Thr Asn Cys Met Glu Ala Gly Arg Val Lys
                85                  90                  95

Cys Glu His Tyr Trp Pro Leu Asp Ser Gln Pro Cys Thr His Gly His
            100                 105                 110

Leu Arg Val Thr Leu Val Gly Glu Val Met Glu Asn Trp Thr Val
        115                 120                 125

Leu Leu Leu Leu Gln Val Glu Glu Gln Lys Thr Leu Ser Val Arg Gln
    130                 135                 140

Phe His Tyr Gln Ala Trp Pro Asp His Gly Val Pro Ser Ser Pro Asp
145                 150                 155                 160

Thr Leu Leu Ala Phe Trp Arg Met Leu Arg Gln Trp Leu Asp Gln Thr
                165                 170                 175

Met Glu Gly Gly Pro Pro Ile Val His Cys Ser Ala Gly Val Gly Arg
            180                 185                 190

Thr Gly Thr Leu Ile Ala Leu Asp Val Leu Leu Arg Gln Leu Gln Ser
        195                 200                 205

Glu Gly Leu Leu Gly Pro Phe Ser Phe Val Arg Lys Met Arg Glu Ser
    210                 215                 220

Arg Pro Leu Met Val Gln Thr Glu Ala Gln Tyr Val Phe Leu His Gln
225                 230                 235                 240

Cys Ile Cys Gly Ser Ser Asn Ser Gln Pro Arg Pro Gln Pro Arg
                245                 250                 255
```

(2) INFORMATION FOR SEQ ID NO:17:

(i) SEQUENCE CHARACTERISTICS:
        (A) LENGTH: 243 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Phe Val Asp Pro Lys Glu Tyr Asp Ile Pro Gly Leu Val Arg Lys Asn
1               5                   10                  15

Arg Tyr Lys Thr Ile Leu Pro Asn Pro His Ser Arg Val Arg Leu Thr
            20                  25                  30

Ser Pro Asp Pro Glu Asp Pro Leu Ser Ser Tyr Ile Asn Ala Asn Tyr
        35                  40                  45
```

-continued

```
Ile Arg Gly Tyr Asn Gly Glu Glu Lys Val Tyr Ile Ala Thr Gln Gly
 50                  55                  60

Pro Ile Val Ser Thr Val Val Asp Phe Trp Arg Met Val Trp Gln Glu
 65                  70                  75                  80

Arg Thr Pro Ile Ile Val Met Ile Thr Asn Ile Glu Glu Met Asn Glu
                 85                  90                  95

Lys Cys Thr Glu Tyr Trp Pro Glu Glu Gln Val Val His Asp Gly Val
            100                 105                 110

Glu Ile Thr Val Gln Lys Val Ile His Thr Glu Asp Tyr Arg Leu Ile
        115                 120                 125

Ser Leu Arg Arg Gly Thr Glu Glu Arg Gly Leu Lys His Tyr Trp Phe
130                 135                 140

Thr Ser Trp Pro Asp Gln Lys Thr Pro Asp Arg Ala Pro Pro Leu Leu
145                 150                 155                 160

His Leu Val Arg Glu Val Glu Glu Ala Ala Gln Gln Glu Gly Pro His
                165                 170                 175

Cys Ser Pro Ile Ile Val His Cys Ser Ala Gly Ile Gly Arg Thr Gly
            180                 185                 190

Cys Phe Ile Ala Thr Ser Ile Cys Cys Gln Gln Leu Arg Arg Glu Gly
        195                 200                 205

Val Val Asp Ile Leu Lys Thr Thr Cys Gln Leu Arg Gln Asp Arg Gly
210                 215                 220

Gly Met Ile Gln Thr Cys Glu Gln Tyr Gln Phe Val His His Ala Met
225                 230                 235                 240

Ser Leu Tyr
```

(2) INFORMATION FOR SEQ ID NO:18:

(i) SEQUENCE CHARACTERISTICS:
        (A) LENGTH: 257 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Asp Arg Thr Thr Lys Asn Ser Asp Leu Lys Glu Asn Ala Cys Lys Asn
  1               5                  10                  15

Arg Tyr Pro Asp Ile Lys Ala Tyr Asp Gln Thr Arg Val Lys Leu Ala
                 20                  25                  30

Val Ile Asn Gly Leu Gln Thr Thr Asp Tyr Ile Asn Ala Asn Phe Val
            35                  40                  45

Ile Gly Tyr Lys Glu Arg Lys Lys Phe Ile Cys Ala Gln Gly Pro Met
 50                  55                  60

Glu Ser Thr Ile Asp Asp Phe Trp Arg Met Ile Trp Glu Gln His Leu
 65                  70                  75                  80

Glu Ile Ile Val Ile Leu Thr Asn Leu Glu Glu Tyr Asn Lys Ala Lys
                 85                  90                  95

Cys Ala Lys Tyr Trp Pro Glu Lys Val Phe Asp Thr Lys Gln Phe Gly
            100                 105                 110

Asp Ile Leu Val Lys Phe Ala Gln Glu Arg Lys Thr Gly Asp Tyr Ile
        115                 120                 125

Glu Leu Asn Val Ser Lys Asn Lys Ala Asn Val Gly Glu Glu Glu Asp
130                 135                 140

Arg Arg Gln Ile Thr Gln Tyr His Tyr Leu Thr Trp Lys Asp Phe Met
145                 150                 155                 160
```

```
Ala Pro Glu His Pro His Gly Ile Ile Lys Phe Ile Arg Gln Ile Asn
                165                 170                 175

Ser Val Tyr Ser Leu Gln Arg Gly Pro Ile Leu Val His Cys Ser Ala
            180                 185                 190

Gly Val Gly Arg Thr Gly Thr Leu Val Ala Leu Asp Ser Leu Ile Gln
        195                 200                 205

Gln Leu Glu Glu Glu Asp Ser Val Ser Ile Tyr Asn Thr Val Cys Asp
    210                 215                 220

Leu Arg His Gln Arg Asn Phe Leu Val Gln Ser Leu Lys Gln Tyr Ile
225                 230                 235                 240

Phe Leu Tyr Arg Ala Leu Leu Asp Thr Gly Thr Phe Gly Asn Thr Asp
                245                 250                 255

Ile
```

(2) INFORMATION FOR SEQ ID NO:19:

(i) SEQUENCE CHARACTERISTICS:
        (A) LENGTH: 258 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Val Gly Thr Phe His Cys Ser Met Ser Pro Gly Asn Leu Glu Lys Asn
1               5                   10                  15

Arg Tyr Gly Asp Val Pro Cys Leu Asp Gln Thr Arg Val Lys Leu Thr
            20                  25                  30

Lys Arg Ser Gly His Thr Gln Thr Asp Tyr Ile Asn Ala Ser Phe Met
        35                  40                  45

Asp Gly Tyr Lys Gln Lys Asn Ala Tyr Ile Gly Thr Gln Gly Pro Leu
    50                  55                  60

Glu Asn Thr Tyr Arg Asp Phe Trp Leu Met Val Trp Glu Gln Lys Val
65                  70                  75                  80

Leu Val Ile Val Met Thr Thr Arg Phe Glu Glu Gly Gly Arg Arg Lys
                85                  90                  95

Cys Gly Gln Tyr Trp Pro Leu Glu Lys Asp Ser Arg Ile Arg Phe Gly
                100                 105                 110

Phe Leu Thr Val Thr Asn Leu Gly Val Glu Asn Met Asn His Tyr Lys
            115                 120                 125

Lys Leu Glu Ile His Asn Thr Glu Glu Arg Gln Lys Arg Gln Val Thr
        130                 135                 140

His Phe Gln Phe Leu Ser Trp Pro Asp Tyr Gly Val Pro Ser Ser Ala
145                 150                 155                 160

Ala Ser Leu Ile Asp Phe Leu Arg Val Val Arg Asn Gln Gln Ser Leu
                165                 170                 175

Ala Val Ser Asn Met Gly Ala Arg Ser Lys Gly Gln Cys Pro Glu Pro
            180                 185                 190

Pro Ile Val Val His Cys Ser Ala Gly Ile Gly Arg Thr Gly Thr Phe
        195                 200                 205

Cys Ser Leu Asp Ile Cys Leu Ala Gln Leu Glu Glu Leu Gly Thr Leu
    210                 215                 220

Asn Val Phe Gln Thr Val Ser Arg Met Arg Thr Gln Arg Ala Phe Ser
225                 230                 235                 240

Ile Gln Thr Pro Glu Gln Tyr Tyr Phe Cys Tyr Lys Ala Ile Leu Glu
```

245              250             255

Phe Ala (2) INFORMATION FOR SEQ ID NO:20:

(i) SEQUENCE CHARACTERISTICS:
        (A) LENGTH: 253 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Ile Tyr Pro Thr Ala Thr Gly Glu Lys Glu Asn Val Lys Lys Asn
1               5                   10                  15

Arg Tyr Lys Asp Ile Leu Pro Phe Asp His Ser Arg Val Lys Leu Thr
            20                  25                  30

Leu Lys Thr Pro Ser Gln Asp Ser Asp Tyr Ile Asn Ala Asn Phe Ile
                35                  40                  45

Lys Gly Val Tyr Gly Pro Lys Ala Tyr Val Ala Thr Gln Gly Pro Leu
    50                  55                  60

Ala Asn Thr Val Ile Asp Phe Trp Arg Met Val Trp Glu Tyr Asn Val
65                  70                  75                  80

Val Ile Ile Val Met Ala Cys Arg Glu Phe Glu Met Gly Arg Lys Lys
                85                  90                  95

Cys Glu Arg Tyr Trp Pro Leu Tyr Gly Glu Asp Pro Ile Thr Phe Ala
                100                 105                 110

Pro Phe Lys Ile Ser Cys Glu Asp Glu Gln Ala Arg Thr Asp Tyr Phe
            115                 120                 125

Ile Leu Leu Leu Glu Phe Gln Asn Glu Ser Arg Arg Leu Tyr Gln Phe
130                 135                 140

His Tyr Val Asn Trp Pro Asp His Asp Val Pro Ser Ser Phe Asp Ser
145                 150                 155                 160

Ile Leu Asp Met Ile Ser Leu Met Arg Lys Tyr Gln Glu His Glu Asp
                165                 170                 175

Val Pro Ile Cys Ile His Cys Ser Ala Gly Cys Gly Arg Thr Gly Ala
            180                 185                 190

Ile Cys Ala Ile Asp Tyr Thr Trp Asn Leu Leu Lys Ala Gly Lys Ile
        195                 200                 205

Pro Glu Glu Phe Asn Val Phe Asn Leu Ile Gln Glu Met Arg Thr Gln
    210                 215                 220

Arg His Ser Ala Val Gln Thr Lys Glu Gln Tyr Glu Leu Val His Arg
225                 230                 235                 240

Ala Ile Ala Gln Leu Phe Glu Lys Gln Leu Gln Leu Tyr
                245                 250

(2) INFORMATION FOR SEQ ID NO:21:

(i) SEQUENCE CHARACTERISTICS:
        (A) LENGTH: 242 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Gly Leu Ala Ile Thr Phe Ala Lys Leu Pro Gln Asn Leu Asp Lys Asn
1               5                   10                  15

```
Arg Tyr Lys Asp Val Leu Pro Tyr Asp Thr Thr Arg Val Leu Leu Gln
            20                  25                  30

Gly Asn Glu Asp Tyr Ile Asn Ala Ser Tyr Val Asn Met Glu Ile Pro
            35                  40                  45

Ala Ala Asn Leu Val Asn Lys Tyr Ile Ala Thr Gln Gly Pro Leu Pro
 50                  55                  60

His Thr Cys Ala Gln Phe Trp Gln Val Val Trp Asp Gln Lys Leu Ser
 65                  70                  75                  80

Leu Ile Val Met Leu Thr Thr Leu Thr Glu Arg Gly Arg Thr Lys Cys
                 85                  90                  95

His Gln Tyr Trp Pro Asp Pro Asp Val Met Asn His Gly Gly Phe
                100                 105                 110

His Ile Gln Cys Gln Ser Glu Asp Cys Thr Ile Ala Tyr Val Ser Met
                115                 120                 125

Leu Val Thr Asn Thr Gln Thr Gly Glu Glu His Thr Val Thr His Leu
            130                 135                 140

Gln Tyr Val Ala Trp Pro Asp His Gly Ile Pro Asp Ser Ser Asp
145                 150                 155                 160

Phe Leu Glu Phe Val Asn Tyr Val Arg Ser Leu Arg Val Asp Ser Glu
                165                 170                 175

Pro Val Leu Val His Cys Ser Ala Gly Ile Gly Arg Thr Gly Val Leu
                180                 185                 190

Val Thr Met Glu Thr Ala Met Cys Leu Thr Glu Arg Asn Leu Pro Ile
            195                 200                 205

Tyr Pro Leu Asp Ile Val Arg Lys Met Arg Asp Gln Arg Ala Met Met
            210                 215                 220

Val Gln Thr Ser Ser Gln Tyr Lys Phe Val Cys Glu Ala Ile Leu Arg
225                 230                 235                 240

Val Tyr (2) INFORMATION FOR SEQ ID NO:22:

(i) SEQUENCE CHARACTERISTICS:
        (A) LENGTH: 277 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Pro Ser Glu Thr Ser Glu Gly Asp Lys Lys His Asn Thr Ser Lys Asn
 1               5                  10                  15

Arg Tyr Thr Asn Ile Leu Pro Val Asn His Thr Arg Val Gln Leu Lys
            20                  25                  30

Lys Ile Gln Asp Lys Glu Gly Ser Asp Tyr Ile Asn Ala Asn Tyr Ile
            35                  40                  45

Asp Gly Ala Tyr Pro Lys Gln Phe Ile Cys Thr Gln Gly Pro Leu Pro
 50                  55                  60

Asn Thr Ile Ala Asp Phe Trp Arg Met Val Trp Glu Asn Arg Cys Arg
 65                  70                  75                  80

Ile Ile Val Met Leu Ser Arg Glu Ser Glu Gly Ser Glu Asn Cys Arg
                 85                  90                  95

Ile Lys Cys Asp Arg Tyr Trp Pro Glu Gln Ile Gly Gly Glu Gln Phe
                100                 105                 110

Ser Ile Tyr Gly Asn Gly Asn Glu Val Phe Gly Thr Tyr Ser Val Glu
```

```
                    115                 120                 125
Leu Val Glu Val Ile Gln Cys Arg Glu Ile Ile Thr Arg Asn Ile Arg
    130                 135                 140
Leu Thr Phe Glu Gly Glu Thr Arg Asp Ile Thr Gln Tyr Gln Tyr Glu
145                 150                 155                 160
Gly Trp Pro Asp His Asn Ile Pro Asp His Thr Gln Pro Phe Arg Gln
                165                 170                 175
Leu Leu His Ser Ile Thr Asn Arg Gln Asn Gln Ile Ile Pro Ser Ser
                180                 185                 190
Asp Arg Asn Val Pro Ile Ile Val His Cys Ser Ala Gly Val Gly Arg
            195                 200                 205
Thr Gly Thr Phe Cys Thr Ala Val Ile Met Met Lys Lys Leu Asp His
        210                 215                 220
Tyr Phe Lys Gln Leu Asp Tyr Asn Ser Arg Ile Asp Phe Asn Leu Phe
225                 230                 235                 240
Ser Ile Val Leu Lys Leu Arg Glu Gln Arg Pro Gly Met Val Gln Gln
                245                 250                 255
Leu Glu Gln Tyr Leu Phe Cys Tyr Lys Thr Ile Leu Asp Glu Ile Tyr
            260                 265                 270
His Arg Leu Asn Cys
            275

(2) INFORMATION FOR SEQ ID NO:23:

(i) SEQUENCE CHARACTERISTICS:
        (A) LENGTH: 254 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Gln Trp Ser Thr Val Asp Ser Leu Ser Asn Thr Ser Tyr Lys Lys Asn
1               5                   10                  15
Arg Tyr Thr Asp Ile Val Pro Tyr Asn Cys Thr Arg Val His Leu Lys
                20                  25                  30
Arg Thr Ser Pro Ser Glu Leu Asp Tyr Ile Asn Ala Ser Phe Ile Lys
            35                  40                  45
Thr Glu Thr Ser Asn Tyr Ile Ala Cys Gln Gly Ser Ile Ser Arg Ser
50                  55                  60
Ile Ser Asp Phe Trp His Met Val Trp Asp Asn Val Glu Asn Ile Gly
65              70                  75                  80
Thr Ile Val Met Leu Gly Ser Leu Phe Glu Ala Gly Arg Glu Met Cys
                85                  90                  95
Thr Ala Tyr Trp Pro Ser Asn Gly Ile Gly Asp Lys Gln Val Tyr Gly
            100                 105                 110
Asp Tyr Cys Val Lys Gln Ile Ser Glu Glu Asn Val Asp Asn Ser Arg
        115                 120                 125
Phe Ile Leu Phe Glu Ile Gln Asn Ala Asn Phe Pro Ser Val Lys Lys
    130                 135                 140
Val His His Tyr Gln Tyr Pro Asn Trp Ser Asp Cys Asn Ser Pro Glu
145                 150                 155                 160
Asn Val Lys Ser Met Val Glu Phe Leu Lys Tyr Val Asn Asn Ser His
                165                 170                 175
Gly Ser Gly Asn Thr Ile Val His Cys Ser Ala Gly Val Gly Arg Thr
            180                 185                 190
```

Gly Thr Phe Ile Val Leu Asp Thr Ile Leu Arg Phe Pro Glu Ser Lys
            195                 200                 205

Leu Ser Gly Phe Asn Pro Ser Val Ala Asp Ser Ser Asp Val Val Phe
        210                 215                 220

Gln Leu Val Asp His Ile Arg Lys Gln Arg Met Lys Met Val Gln Thr
225                 230                 235                 240

Phe Thr Gln Phe Lys Tyr Val Tyr Asp Leu Ile Asp Ser Leu
                245                 250

(2) INFORMATION FOR SEQ ID NO:24:

(i) SEQUENCE CHARACTERISTICS:
        (A) LENGTH: 250 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Trp Cys Cys Leu Ala Ser Ser Arg Ser Thr Ser Ile Ser Arg Lys Asn
1               5                   10                  15

Arg Tyr Thr Asp Ile Val Pro Tyr Asp Lys Thr Arg Val Arg Leu Ala
                20                  25                  30

Val Pro Lys Gly Cys Ser Asp Tyr Ile Asn Ala Ser His Ile Asp Val
            35                  40                  45

Gly Asn Lys Lys Tyr Ile Ala Cys Gln Ala Pro Lys Pro Gly Thr Leu
        50                  55                  60

Leu Asp Phe Trp Glu Met Val Trp His Asn Ser Gly Thr Asn Gly Val
65                  70                  75                  80

Ile Val Met Leu Thr Asn Leu Tyr Glu Ala Gly Ser Glu Lys Cys Ser
                85                  90                  95

Gln Tyr Trp Pro Asp Asn Lys Asp His Ala Leu Cys Leu Glu Gly Gly
                100                 105                 110

Leu Arg Ile Ser Val Gln Lys Tyr Glu Thr Phe Glu Asp Leu Lys Val
            115                 120                 125

His Leu Phe Arg Leu Asp Lys Pro Asn Gly Pro Pro Lys Tyr Ile His
        130                 135                 140

His Phe Trp Val His Thr Trp Phe Asp Lys Thr His Pro Asp Ile Glu
145                 150                 155                 160

Ser Ile Thr Gly Leu Ile Arg Cys Ile Asp Lys Val Pro Asn Asp Gly
                165                 170                 175

Pro Met Phe Val His Cys Ser Ala Gly Val Gly Arg Thr Gly Thr Phe
            180                 185                 190

Ile Ala Val Asp Gln Ile Leu Gln Val Pro Lys Asn Ile Leu Pro Lys
        195                 200                 205

Thr Thr Asn Leu Glu Asp Ser Lys Asp Phe Ile Phe Asn Cys Val Asn
210                 215                 220

Ser Leu Arg Ser Gln Arg Met Lys Met Val Gln Asn Phe Glu Gln Phe
225                 230                 235                 240

Lys Phe Leu Tyr Asp Val Val Asp Tyr Leu
                245                 250

(2) INFORMATION FOR SEQ ID NO:25:

(i) SEQUENCE CHARACTERISTICS:
        (A) LENGTH: 260 amino acids
        (B) TYPE: amino acid (C) STRANDEDNESS: single
(D) TOPOLOGY: linear (ii) MOLECULE TYPE: peptide (xi) SEQUENCE DESCRIPTION: SEQ ID NO:25:

| | | | | | | | | | | | | | | |
|---|---|---|---|---|---|---|---|---|---|---|---|---|---|---|
|Gly|Ile|Thr|Ala|Asp|Ser|Ser|Asn|His|Pro|Asp|Asn|Lys|His|Lys|Asn
|1| | | |5| | | | |10| | | | |15|

Arg Tyr Ile Asn Ile Val Ala Tyr Asp His Ser Arg Val Lys Leu Ala
          20                  25                  30

Gln Leu Ala Glu Lys Asp Gly Lys Leu Thr Asp Tyr Ile Asn Ala Asn
              35                  40                  45

Tyr Val Asp Gly Tyr Asn Arg Pro Lys Ala Tyr Ile Ala Ala Gln Gly
    50                  55                  60

Pro Leu Lys Ser Thr Ala Glu Asp Phe Trp Arg Met Ile Trp Glu His
65                  70                  75                  80

Asn Val Glu Val Ile Val Met Ile Thr Asn Leu Val Glu Lys Gly Arg
                85                  90                  95

Arg Lys Cys Asp Gln Tyr Trp Pro Ala Asp Gly Ser Glu Glu Tyr Gly
            100                 105                 110

Asn Phe Leu Val Thr Gln Lys Ser Val Gln Val Leu Ala Tyr Tyr Thr
            115                 120                 125

Val Phe Thr Leu Arg Asn Thr Lys Ile Lys Lys Gly Ser Gln Lys Gly
            130                 135                 140

Arg Pro Ser Gly Arg Val Val Thr Gln Tyr His Tyr Thr Gln Trp Pro
145                 150                 155                 160

Asp Met Gly Val Pro Glu Tyr Ser Leu Pro Val Leu Thr Phe Val Arg
                165                 170                 175

Lys Ala Ala Tyr Ala Lys Arg His Ala Val Gly Pro Val Val Val His
                180                 185                 190

Cys Ser Ala Gly Val Gly Arg Thr Gly Thr Tyr Ile Val Leu Asp Ser
            195                 200                 205

Met Leu Gln Gln Ile Gln His Glu Gly Thr Val Asn Ile Phe Gly Phe
            210                 215                 220

Leu Lys His Ile Arg Ser Gln Arg Asn Tyr Leu Val Gln Thr Glu Glu
225                 230                 235                 240

Gln Tyr Val Phe Ile His Asp Thr Leu Val Glu Ala Ile Leu Ser Lys
                245                 250                 255

Glu Thr Glu Val
            260

(2) INFORMATION FOR SEQ ID NO:26:

(i) SEQUENCE CHARACTERISTICS:
        (A) LENGTH: 245 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Thr Ser Arg Phe Ile Ser Ala Asn Leu Pro Cys Asn Lys Phe Lys Asn
1                   5                   10                  15

Arg Leu Val Asn Ile Met Pro Tyr Glu Leu Thr Arg Val Cys Leu Gln
            20                  25                  30

Pro Ile Arg Gly Val Glu Gly Ser Asp Tyr Ile Asn Ala Ser Phe Leu
            35                  40                  45

```
Asp Gly Tyr Arg Gln Gln Lys Ala Tyr Ile Ala Thr Gln Gly Pro Leu
 50                  55                  60

Ala Glu Ser Thr Glu Asp Phe Trp Arg Met Leu Trp Glu His Asn Ser
 65                  70                  75                  80

Thr Ile Ile Val Met Leu Thr Lys Leu Arg Glu Met Gly Arg Glu Lys
                 85                  90                  95

Cys His Gln Tyr Trp Pro Ala Glu Arg Ser Ala Arg Tyr Gln Tyr Phe
                100                 105                 110

Val Val Asp Pro Met Ala Glu Tyr Asn Met Pro Gln Tyr Ile Leu Phe
            115                 120                 125

Lys Val Thr Asp Ala Arg Asp Gly Gln Ser Arg Thr Ile Arg Gln Phe
            130                 135                 140

Gln Phe Thr Asp Trp Pro Glu Gln Gly Val Pro Lys Thr Gly Glu Gly
145                 150                 155                 160

Phe Ile Asp Phe Ile Gly Gln Val His Lys Thr Lys Glu Gln Phe Gly
                165                 170                 175

Gln Asp Gly Pro Ile Thr Val His Cys Ser Ala Gly Val Gly Arg Thr
                180                 185                 190

Gly Val Phe Ile Thr Leu Ser Ile Val Leu Glu Arg Met Arg Tyr Glu
            195                 200                 205

Gly Val Val Asp Met Phe Gln Thr Val Lys Thr Leu Arg Thr Gln Arg
            210                 215                 220

Pro Ala Met Val Gln Thr Glu Asp Gln Tyr Gln Leu Cys Tyr Arg Ala
225                 230                 235                 240

Ala Leu Glu Tyr Leu
                245

(2) INFORMATION FOR SEQ ID NO:27:

(i) SEQUENCE CHARACTERISTICS:
        (A) LENGTH: 232 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Asn Asp Lys Met Arg Thr Gly Asn Leu Pro Ala Asn Met Lys Lys Asn
 1               5                  10                  15

Arg Val Leu Gln Ile Ile Pro Tyr Glu Phe Asn Arg Val Ile Ile Pro
                 20                  25                  30

Val Lys Arg Gly Glu Asn Asp Lys Met Arg Thr Gly Asn Leu Pro Ala
             35                  40                  45

Asn Met Lys Lys Asn Arg Val Leu Gln Ile Ile Pro Tyr Glu Phe Asn
 50                  55                  60

Arg Val Ile Ile Pro Val Lys Arg Gly Glu Glu Asn Thr Asp Tyr Val
 65                  70                  75                  80

Asn Ala Ser Phe Ile Asp Gly Tyr Arg Gln Lys Asp Ser Tyr Ile Ala
                 85                  90                  95

Ser Gln Gly Pro Leu Leu His Thr Ile Glu Asp Phe Trp Arg Met Ile
                100                 105                 110

Trp Glu Trp Lys Ser Cys Ser Ile Val Met Leu Thr Glu Leu Glu Glu
            115                 120                 125

Arg Gly Gln Glu Lys Cys Ala Gln Tyr Trp Pro Ser Asp Gly Leu Val
            130                 135                 140

Ser Tyr Gly Asp Ile Thr Val Glu Leu Lys Lys Glu Glu Glu Cys Glu
```

```
 145                 150                 155                 160
Ser Tyr Thr Val Leu Val Thr Asn Thr Arg Glu Asn Lys Ser Arg
                165                 170                 175

Gln Ile Arg Gln Phe His Phe His Gly Trp Pro Glu Val Gly Ile Pro
            180                 185                 190

Ser Asp Gly Lys Gly Met Ile Ser Ile Ile Ala Ala Val Gln Lys Gln
        195                 200                 205

Gln Gln Gln Ser Gly Asn His Pro Ile Thr Val His Cys Ser Ala Gly
    210                 215                 220

Ala Gly Arg Thr Gly Thr Phe Cys
225                 230

(2) INFORMATION FOR SEQ ID NO:28:

(i) SEQUENCE CHARACTERISTICS:
        (A) LENGTH: 249 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Lys Glu Asn Met Arg Thr Gly Asn Leu Pro Ala Asn Met Lys Lys Ala
1               5                   10                  15

Arg Val Ile Gln Ile Ile Pro Tyr Asp Phe Asn Arg Val Ile Leu Ser
            20                  25                  30

Met Lys Arg Gly Gln Glu Tyr Thr Asp Tyr Ile Asn Ala Ser Phe Ile
        35                  40                  45

Asp Gly Tyr Arg Gln Lys Asp Tyr Phe Ile Ala Thr Gln Gly Pro Leu
    50                  55                  60

Ala His Thr Val Glu Asp Phe Trp Arg Met Ile Trp Glu Trp Lys Ser
65                  70                  75                  80

His Thr Ile Val Met Leu Thr Glu Val Gln Glu Arg Glu Gln Asp Lys
                85                  90                  95

Cys Tyr Gln Tyr Trp Pro Thr Glu Gly Ser Val Thr His Gly Glu Ile
            100                 105                 110

Thr Ile Glu Ile Lys Asn Asp Thr Leu Ser Glu Ala Ile Ser Ile Phe
        115                 120                 125

Leu Val Thr Leu Asn Gln Pro Gln Ala Arg Gln Glu Glu Gln Val Arg
    130                 135                 140

Val Val Arg Gln Phe His Phe His Gly Trp Pro Glu Ile Gly Ile Pro
145                 150                 155                 160

Ala Glu Gly Lys Gly Met Ile Asp Leu Ile Ala Ala Val Gln Lys Gln
                165                 170                 175

Gln Gln Gln Thr Gly Asn His Pro Ile Thr Val His Cys Ser Ala Gly
            180                 185                 190

Ala Gly Arg Thr Gly Thr Phe Ile Ala Leu Ser Asn Ile Leu Glu Arg
        195                 200                 205

Val Lys Ala Glu Gly Leu Leu Asp Val Phe Gln Ala Val Lys Ser Leu
    210                 215                 220

Arg Leu Gln Arg Pro His Met Val Gln Thr Leu Glu Gln Tyr Glu Phe
225                 230                 235                 240

Cys Tyr Lys Val Val Gln Asp Phe Ile
                245

(2) INFORMATION FOR SEQ ID NO:29:
```

(i) SEQUENCE CHARACTERISTICS:
    (A) LENGTH: 249 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:29:

```
Val Glu Asp Cys Ser Ile Ala Leu Leu Pro Arg Asn His Glu Lys Asn
1               5                   10                  15

Arg Cys Met Asp Ile Leu Pro Pro Asp Arg Cys Leu Pro Phe Leu Ile
            20                  25                  30

Thr Ile Asp Gly Glu Ser Ser Asn Tyr Ile Asn Ala Ala Leu Met Asp
            35                  40                  45

Ser Tyr Lys Gln Pro Ser Ala Phe Ile Val Thr Gln His Pro Leu Pro
50                  55                  60

Asn Thr Val Lys Asp Phe Trp Arg Leu Val Leu Asp Tyr His Cys Thr
65                  70                  75                  80

Ser Val Val Met Leu Asn Asp Val Asp Pro Ala Gln Leu Cys Pro Gln
                85                  90                  95

Tyr Trp Pro Glu Asn Gly Val His Arg His Gly Pro Ile Gln Val Glu
                100                 105                 110

Phe Val Ser Ala Asp Leu Glu Glu Asp Ile Ile Ser Phe Arg Ile Tyr
            115                 120                 125

Asn Ala Ala Arg Pro Gln Asp Gly Tyr Arg Met Val Gln Gln Phe Gln
            130                 135                 140

Phe Leu Gly Trp Pro Met Tyr Arg Asp Thr Pro Val Ser Lys Arg Ser
145                 150                 155                 160

Phe Leu Lys Leu Ile Arg Gln Val Asp Lys Trp Gln Glu Glu Tyr Asn
                165                 170                 175

Gly Gly Glu Gly Pro Thr Val Val His Cys Leu Asn Gly Gly Gly Arg
                180                 185                 190

Ser Gly Thr Phe Cys Ala Ile Ser Ile Val Cys Glu Met Leu Arg His
            195                 200                 205

Gln Arg Thr Val Asp Val Phe His Ala Val Lys Thr Leu Arg Asn Asn
            210                 215                 220

Lys Pro Asn Met Val Asp Leu Leu Asp Gln Tyr Lys Phe Cys Tyr Glu
225                 230                 235                 240

Val Ala Leu Glu Tyr Leu Asn Ser Gly
                245
```

(2) INFORMATION FOR SEQ ID NO:30:

(i) SEQUENCE CHARACTERISTICS:
    (A) LENGTH: 277 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:30:

```
Trp Arg Thr Gln His Ile Gly Asn Gln Glu Glu Asn Lys Lys Lys Asn
1               5                   10                  15

Arg Asn Ser Asn Val Val Pro Tyr Asp Phe Asn Arg Val Pro Leu Lys
            20                  25                  30

His Glu Leu Glu Met Ser Lys Glu Ser Glu Pro Glu Ser Asp Glu Ser
            35                  40                  45
```

Ser Asp Asp Asp Ser Asp Ser Glu Glu Thr Ser Lys Tyr Ile Asn Ala
    50                  55                  60

Ser Phe Val Met Ser Tyr Trp Lys Pro Glu Met Met Ile Ala Ala Gln
 65              70                  75                      80

Gly Pro Leu Lys Glu Thr Ile Gly Asp Phe Trp Gln Met Ile Phe Gln
                85                  90                  95

Arg Lys Val Lys Val Ile Val Met Leu Thr Glu Leu Val Asn Gly Asp
            100                 105                 110

Gln Glu Val Cys Ala Gln Tyr Trp Gly Glu Gly Lys Gln Thr Tyr Gly
            115                 120                 125

Asp Met Glu Val Glu Met Lys Asp Thr Asn Arg Ala Ser Ala Tyr Thr
        130                 135                 140

Leu Phe Glu Leu Arg His Ser Lys Arg Lys Glu Pro Arg Thr Val Tyr
145                 150                 155                 160

Gln Tyr Gln Cys Thr Thr Trp Lys Gly Glu Glu Leu Pro Ala Glu Pro
                165                 170                 175

Lys Asp Leu Val Ser Met Ile Gln Asp Leu Lys Gln Lys Leu Pro Lys
            180                 185                 190

Ala Ser Pro Glu Gly Met Lys Tyr His Lys His Ala Ser Ile Leu Val
            195                 200                 205

His Cys Arg Asp Gly Ser Gln Gln Thr Gly Leu Phe Cys Ala Leu Phe
            210                 215                 220

Asn Leu Leu Glu Ser Ala Glu Thr Glu Asp Val Val Asp Val Phe Gln
225                 230                 235                 240

Val Val Lys Ser Leu Arg Lys Ala Arg Pro Gly Val Val Cys Ser Tyr
                245                 250                 255

Glu Gln Tyr Gln Phe Leu Tyr Asp Ile Ile Ala Ser Ile Tyr Pro Ala
                260                 265                 270

Gln Asn Gly Gln Val
            275

(2) INFORMATION FOR SEQ ID NO:31:

(i) SEQUENCE CHARACTERISTICS:
        (A) LENGTH: 247 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

Ser Lys Ser Cys Ser Val Gly Glu Asn Glu Glu Asn Met Lys Lys Asn
 1               5                  10                  15

Arg Ser Gln Glu Ile Ile Pro Tyr Asp Arg Asn Arg Val Ile Leu Thr
             20                  25                  30

Pro Leu Pro Met Arg Glu Asn Ser Thr Tyr Ile Asn Ala Ser Phe Ile
         35                  40                  45

Glu Gly Tyr Asp Asn Ser Glu Thr Phe Ile Ile Ala Gln Asp Pro Phe
     50                  55                  60

Glu Asn Thr Ile Gly Asp Phe Trp Arg Met Ile Ser Glu Gln Ser Val
 65                  70                  75                  80

Thr Thr Leu Val Met Ile Ser Glu Ile Gly Asp Gly Pro Arg Lys Cys
                 85                  90                  95

Pro Arg Tyr Trp Ala Asp Asp Glu Val Gln Tyr Asp His Ile Leu Val
            100                 105                 110

```
Lys Tyr Val His Ser Glu Ser Cys Pro Tyr Tyr Thr Phe Phe Tyr Val
            115                 120                 125

Thr Asn Cys Lys Ile Asp Asp Thr Leu Lys Val Thr Gln Phe Gln Tyr
130                 135                 140

Asn Gly Trp Pro Thr Val Asp Gly Glu Val Pro Glu Val Cys Arg Gly
145                 150                 155                 160

Ile Ile Glu Leu Val Asp Gln Ala Tyr Asn His Tyr Lys Asn Asn Lys
                165                 170                 175

Asn Ser Gly Cys Arg Ser Pro Leu Thr Val His Cys Ser Leu Gly Thr
            180                 185                 190

Asp Arg Ser Ser Ile Phe Val Ala Met Cys Ile Leu Val Gln His Leu
        195                 200                 205

Arg Leu Glu Lys Cys Val Asp Ile Cys Ala Thr Thr Arg Lys Leu Arg
    210                 215                 220

Ser Gln Arg Thr Gly Leu Ile Asn Ser Tyr Ala Gln Tyr Glu Phe Leu
225                 230                 235                 240

His Arg Ala Ile Ile Asn Tyr
                245

(2) INFORMATION FOR SEQ ID NO:32:

(i) SEQUENCE CHARACTERISTICS:
        (A) LENGTH: 252 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

Gln Ser Asp Tyr Ser Ala Ala Leu Lys Gln Cys Asn Arg Glu Lys Asn
1               5                   10                  15

Arg Thr Ser Ser Ile Ile Pro Val Glu Arg Ser Arg Val Gly Ile Ser
            20                  25                  30

Ser Leu Ser Gly Glu Gly Thr Asp Tyr Ile Asn Ala Ser Tyr Ile Met
        35                  40                  45

Gly Tyr Tyr Gln Ser Asn Glu Phe Ile Ile Thr Gln His Pro Leu Leu
50                  55                  60

His Thr Ile Lys Asp Phe Trp Arg Met Ile Trp Asp His Asn Ala Gln
65                  70                  75                  80

Leu Val Val Met Ile Pro Asp Gly Gln Asn Met Ala Glu Asp Glu Phe
                85                  90                  95

Val Tyr Trp Pro Asn Lys Asp Glu Pro Ile Asn Cys Glu Ser Phe Lys
            100                 105                 110

Val Thr Leu Met Ala Glu Glu His Lys Cys Leu Ser Asn Glu Glu Lys
        115                 120                 125

Leu Ile Ile Phe Ile Leu Glu Ala Thr Gln Asp Tyr Val Leu Glu
    130                 135                 140

Val Arg His Phe Gln Cys Pro Lys Trp Pro Asn Pro Asp Ser Pro Ile
145                 150                 155                 160

Ser Lys Thr Phe Glu Leu Ile Ser Val Ile Lys Glu Glu Ala Ala Asn
                165                 170                 175

Arg Asp Gly Pro Met Ile Val His Asp Glu His Gly Gly Val Thr Ala
            180                 185                 190

Gly Thr Phe Cys Ala Leu Thr Thr Leu Met His Gln Leu Glu Lys Glu
        195                 200                 205

Asn Ser Val Asp Val Tyr Gln Val Ala Lys Met Ile Asn Leu Met Arg
```

```
            210                 215                 220
Pro Gly Val Phe Ala Asp Ile Glu Gln Tyr Gln Phe Leu Tyr Lys Val
225                 230                 235                 240

Ile Leu Ser Leu Val Ser Thr Arg Gln Glu Glu Asn
                245                 250
```

(2) INFORMATION FOR SEQ ID NO:33:

(i) SEQUENCE CHARACTERISTICS:
        (A) LENGTH: 252 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

```
Val Glu Cys Phe Ser Ala Gln Lys Glu Cys Asn Lys Glu Lys Asn Arg
1               5                   10                  15

Asn Ser Ser Val Val Pro Ser Glu Arg Ala Arg Val Gly Leu Ala Pro
                20                  25                  30

Leu Pro Gly Met Lys Gly Thr Asp Tyr Ile Asn Ala Ser Tyr Ile Met
            35                  40                  45

Gly Tyr Tyr Arg Ser Asn Glu Phe Ile Ile Thr Gln His Pro Leu Pro
        50                  55                  60

His Thr Thr Lys Asp Phe Trp Arg Met Ile Trp Asp His Asn Ala Gln
65                  70                  75                  80

Ile Ile Val Met Leu Pro Asp Asn Gln Ser Leu Ala Glu Asp Glu Phe
                85                  90                  95

Val Tyr Trp Pro Ser Arg Glu Glu Ser Met Asn Cys Glu Ala Phe Thr
                100                 105                 110

Val Thr Leu Ile Ser Lys Asp Arg Leu Cys Leu Ser Asn Glu Glu Gln
            115                 120                 125

Ile Ile Ile Phe Ile Leu Glu Ala Thr Gln Asp Asp Tyr Val Leu Glu
        130                 135                 140

Val Arg His Phe Gln Cys Pro Lys Trp Pro Asn Pro Asp Ala Pro Ile
145                 150                 155                 160

Ser Ser Thr Phe Glu Leu Ile Asn Val Ile Lys Glu Glu Ala Leu Thr
                165                 170                 175

Arg Asp Gly Pro Thr Ile Val His Asp Glu Tyr Gly Ala Val Ser Ala
            180                 185                 190

Gly Met Leu Cys Ala Leu Thr Thr Leu Ser Gln Gln Leu Glu Asn Glu
        195                 200                 205

Asn Ala Val Asp Val Phe Gln Val Ala Lys Met Ile Asn Leu Met Arg
    210                 215                 220

Pro Gly Val Phe Thr Asp Ile Glu Gln Tyr Gln Phe Ile Tyr Lys Ala
225                 230                 235                 240

Met Leu Ser Leu Val Ser Thr Lys Glu Asn Gly Asn
                245                 250
```

(2) INFORMATION FOR SEQ ID NO:34:

(i) SEQUENCE CHARACTERISTICS:
        (A) LENGTH: 278 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

| | | | | | | | | | | | | | | | |
|---|---|---|---|---|---|---|---|---|---|---|---|---|---|---|---|
|Glu|Thr|Asn|Leu|Met|Ala|Glu|Gln|Val|Glu|Leu|Lys|Asn|Cys|Thr| |
|1| | | |5| | | |10| | | |15| | | |
|Pro|Tyr|Leu|Glu|Gln|Gln|Tyr|Lys|Asn|Ile|Ile|Gln|Phe|Gln|Pro|Lys|
| | | |20| | | | |25| | | | |30| | |
|Asp|Ile|His|Ile|Ala|Ser|Ala|Met|Lys|Gln|Val|Asn|Ser|Ile|Lys|Asn|
| | | |35| | | | |40| | | | |45| | |
|Arg|Gly|Ala|Ile|Phe|Pro|Ile|Glu|Gly|Ser|Arg|Val|His|Leu|Thr|Pro|
| | |50| | | | |55| | | | |60| | | |
|Lys|Pro|Gly|Glu|Asp|Gly|Ser|Asp|Tyr|Ile|Asn|Ala|Ser|Trp|Leu|His|
|65| | | | |70| | | | |75| | | | |80|
|Gly|Phe|Arg|Arg|Leu|Arg|Asp|Phe|Ile|Val|Thr|Gln|His|Pro|Met|Ala|
| | | | |85| | | | |90| | | | |95| |
|His|Thr|Ile|Lys|Asp|Phe|Trp|Gln|Met|Val|Trp|Asp|His|Asn|Ala|Gln|
| | | |100| | | | |105| | | | |110| | |
|Thr|Val|Val|Leu|Leu|Ser|Ser|Leu|Asp|Asp|Ile|Asn|Phe|Ala|Gln|Phe|
| | | |115| | | | |120| | | | |125| | |
|Trp|Pro|Asp|Glu|Ala|Thr|Pro|Ile|Glu|Ser|Asp|His|Tyr|Arg|Val|Lys|
| | |130| | | | |135| | | | |140| | | |
|Phe|Leu|Asn|Lys|Thr|Asn|Lys|Ser|Asp|Tyr|Val|Ser|Phe|Val|Ile|Gln|
|145| | | | |150| | | | |155| | | | |160|
|Ser|Ile|Gln|Asp|Asp|Tyr|Glu|Leu|Thr|Val|Lys|Met|Leu|His|Cys|Pro|
| | | | |165| | | | |170| | | | |175| |
|Ser|Trp|Pro|Glu|Met|Ser|Asn|Pro|Asn|Ser|Ile|Tyr|Asp|Phe|Ile|Val|
| | | | |180| | | | |185| | | | |190| |
|Asp|Val|His|Glu|Arg|Cys|Asn|Asp|Tyr|Arg|Asn|Gly|Pro|Ile|Val|Ile|
| | | |195| | | | |200| | | | |205| | |
|Val|Asp|Arg|Tyr|Gly|Gly|Ala|Gln|Ala|Cys|Thr|Phe|Cys|Ala|Ile|Ser|
| | |210| | | | |215| | | | |220| | | |
|Ser|Leu|Ala|Ile|Glu|Met|Glu|Tyr|Cys|Ser|Thr|Ala|Asn|Val|Tyr|Gln|
|225| | | | |230| | | | |235| | | | |240|
|Tyr|Ala|Lys|Leu|Tyr|His|Asn|Lys|Arg|Pro|Gly|Val|Trp|Thr|Ser|Ser|
| | | | |245| | | | |250| | | | |255| |
|Glu|Asp|Ile|Arg|Val|Ile|Tyr|Asn|Ile|Leu|Ser|Phe|Leu|Pro|Gly|Asn|
| | |260| | | | |265| | | | |270| | | |
|Leu|Asn|Leu|Leu|Lys|Arg| | | | | | | | | | |
| | |275| | | | | | | | | | | | | |

(2) INFORMATION FOR SEQ ID NO:35:

(i) SEQUENCE CHARACTERISTICS:
        (A) LENGTH: 243 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

| | | | | | | | | | | | | | | | |
|---|---|---|---|---|---|---|---|---|---|---|---|---|---|---|---|
|Thr|Asn|Asp|Pro|Arg|Tyr|Leu|Gln|Ala|Cys|Gly|Gly|Glu|Lys|Ile|Leu|
|1| | | |5| | | |10| | | |15| | | |
|Asn|Arg|Phe|Arg|Asp|Ile|Gln|Cys|Cys|Arg|Gln|Thr|Ala|Val|Arg|Ala|
| | | |20| | | | |25| | | | |30| | |
|Asp|Asn|Tyr|Ile|Gln|Val|Gly|Asn|Thr|Arg|Thr|Ile|Ala|Cys|Gln|Tyr|
| | | |35| | | | |40| | | | |45| | |
|Pro|Leu|Gln|Ser|Gln|Leu|Glu|Ser|His|Phe|Arg|Met|Leu|Ala|Glu|Asn|
| | |50| | | | |55| | | | |60| | | |

```
Arg Thr Pro Val Leu Ala Val Leu Ala Ser Ser Glu Ile Ala Asn
 65              70                  75                  80

Gln Arg Phe Gly Met Pro Asp Tyr Phe Arg Gln Ser Gly Thr Tyr Gly
                 85                  90                  95

Ser Ile Thr Val Glu Ser Lys Met Thr Gln Gln Val Gly Leu Gly Asp
                100                 105                 110

Gly Ile Asn Met Tyr Thr Leu Thr Ile Arg Glu Ala Gly Gln Lys Thr
            115                 120                 125

Ile Ser Val Pro Val Val His Val Gly Asn Trp Pro Asp Gln Thr Ala
        130                 135                 140

Val Ser Ser Glu Val Thr Lys Ala Leu Ala Ser Leu Val Asp Gln Thr
145                 150                 155                 160

Ala Glu Thr Lys Arg Asn Met Tyr Glu Ser Lys Gly Ser Ser Ala Val
                165                 170                 175

Ala Asp Asp Ser Lys Leu Arg Pro Val Ile His Cys Arg Ala Gly Val
            180                 185                 190

Gly Arg Thr Ala Gln Leu Ile Gly Ala Met Cys Met Asn Asp Ser Arg
        195                 200                 205

Asn Ser Gln Leu Ser Val Glu Asp Met Val Ser Gln Met Arg Val Gln
    210                 215                 220

Arg Asn Gly Met Val Gln Lys Asp Glu Gln Leu Asp Val Leu Ile Lys
225                 230                 235                 240

Leu Ala Glu (2) INFORMATION FOR SEQ ID NO:36:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

Xaa His Cys Xaa Ala Gly Xaa Xaa Arg Xaa Gly
 1               5                  10
```